(12) United States Patent  (10) Patent No.: US 6,422,065 B1
Shine et al.  (45) Date of Patent: Jul. 23, 2002

(54) METHOD FOR TESTING A CELL SAMPLE

(76) Inventors: Thomas Adam Shine, 220 Lawrence St., No. 3, Newhaven, CT (US) 06511; Ian Basil Shine, 444 Central Park West, New York, NY (US) 10025

( * ) Notice: Subject to any disclaimer, the term of this patent is extended or adjusted under 35 U.S.C. 154(b) by 0 days.

(21) Appl. No.: 09/101,013

(22) PCT Filed: Dec. 27, 1996

(86) PCT No.: PCT/GB96/03257

§ 371 (c)(1), (2), (4) Date: Aug. 4, 1998

(87) PCT Pub. No.: WO97/24601

PCT Pub. Date: Jul. 10, 1997

(30) Foreign Application Priority Data

Dec. 29, 1995 (GB) ............................................. 9526649
Dec. 29, 1995 (GB) ............................................. 9526720

(51) Int. Cl.[7] .......................... G06F 19/00; G01N 27/04; G01N 27/00
(52) U.S. Cl. .................... 73/53.01; 73/61.71; 73/865.5; 324/71.1; 324/71.4; 702/21
(58) Field of Search .............................. 324/71.1, 71.4; 377/10, 11, 12; 73/863.21, 863.84, 861, 53.01, 61.55, 61.71, 61.47, 865.5; 702/21

(56) References Cited

U.S. PATENT DOCUMENTS

| 3,502,412 A | | 3/1970 | Burns |
| 3,851,246 A | | 11/1974 | Curby et al. ................... 324/71 |
| 4,081,340 A | | 3/1978 | Zimmermann .............. 204/180 |
| 4,240,027 A | | 12/1980 | Larsen et al. .................. 324/57 |
| 4,271,001 A | | 6/1981 | Imafuku ....................... 204/195 |
| 4,278,936 A | | 7/1981 | Shine ......................... 324/71.1 |
| 4,298,836 A | * | 11/1981 | Groves et al. .............. 324/71.1 |
| 4,374,644 A | | 2/1983 | Armstrong ................. 324/71.4 |
| 4,521,729 A | * | 6/1985 | Kiesewetter et al. ........ 324/71.1 |
| 4,525,666 A | | 6/1985 | Groves ....................... 324/71.1 |
| 4,535,284 A | | 8/1985 | Groves ....................... 324/71.1 |
| 4,791,355 A | * | 12/1988 | Coulter et al. ............. 324/71.1 |
| 4,810,963 A | * | 3/1989 | Blake-Coleman et al. . 324/71.1 |
| 4,876,504 A | * | 10/1989 | Blake et al. ................ 324/71.1 |
| 5,006,460 A | * | 4/1991 | Thomas, Jr. et al. ............ 435/6 |
| 5,464,752 A | * | 11/1995 | Kortright et al. .......... 324/71.1 |
| 5,532,139 A | | 7/1996 | Miller .......................... 435/29 |
| 5,700,632 A | | 12/1997 | Critser et al. .................. 435/2 |
| 5,856,665 A | * | 1/1999 | Price et al. ................. 250/205 |

FOREIGN PATENT DOCUMENTS

| CA | 988319 | * | 5/1976 |
| EP | 001056 | | 4/1980 |

OTHER PUBLICATIONS

Kieler et al. "Spreading of Cells on Various Substrates Evaluated by Fourier Analysis of Shape", Histochemistry, Oct. 1989, vol. 1992, pp. 141–148.*
McLean et al. Life Sciences vol. 6, Sep. 1967, pp. 1983–1986.*
Latimer, Paul Biophysical Journal vol. 27, Jul. 1979, pp. 117–126.*
Bateman, J.B. Journal of Colloid and Interface Science vol. 27, No. 3, Jul. 1968.*
Born, G.V.B. Nature, vol. 194, Jun. 1962, pp. 927–929.*
Remuzzi et al. Biorheology, vol. 21, No. 4, Dec. 1984, pp. 617–630.*

(List continued on next page.)

Primary Examiner—Hezron Williams
Assistant Examiner—Michael Cygan
(74) Attorney, Agent, or Firm—Perman & Green, LLP

(57) ABSTRACT

In this invention, a cell parameter, for example cell volume, is determined by subjecting one or more aliquots of a sample cell suspension to one or more alterations of at least one parameter of the cell environment to identify a point at which the cells achieve a particular shape to obtain a sample specific shape compensation factor. Preferably, the environmental parameter change is a reduction in osmolality.

16 Claims, 16 Drawing Sheets

OTHER PUBLICATIONS

Latimer, Paul Applied Optics, vol. 24, No. 10, Oct. 1975, pp. 2324–2326.*

Bryant et al. Archives of Biochemistry and Biophysics, vol. 135, Dec. 1969, pp. 109–117.*

A Method for Production of $N_2$ Microbubbles in Platelet–Rich Plasma in an Aggregometer–Like Apparatus, and Effect on the Platelet Density in Vitro, T. Thorsen et al. Undersea Biochemical Research vol. 13, Sep. 1986, pp. 271–288.

Cation Permiability and Mechanical Properties of the Erythrocyte Membrane Under the Influence of Lysophoshatidylcholine (LPC) in Isotonic and Hypotonic Media, S. Eskelinen and M. Mela, Acta Physiologica Scandanivica, vol. 122, No. 4, Dec. 1984, pp. 527–534.

Measurement of Biophysical Properties of Red Blood Cells by Resistive Pulse Spectroscopy: Volume, Shape, Surface Area, and Deformability, Gary V. Richieri et al. Journal of Biochemical and Biophysical Methods, 11 (1985) pp. 117–131.

Geometric, osmotic, and membrane mechanical properties of density—separated human red cell. Linderkamp et al. Blood 59 (6), pp. 1121–1127. (Jun. 1992).

* cited by examiner

| N=5 | TIME | Cp | IsoU | Ypk | pko | Real C | Diam | S.I. | Dipth | RBC |
|---|---|---|---|---|---|---|---|---|---|---|
| MEAN | ... | 4.25 | 82.52 | 151.57 | 132.18 | 4987.8 | 6.62 | 14.98 | 1.05 | 2114.9 |
| S.D. | ... | 0.03 | 0.26 | 0.32 | 0.85 | 106.77 | 0.00 | 0.06 | 0.01 | 46.46 |
| S.E. | ... | 0.01 | 0.12 | 0.14 | 0.38 | 47.75 | 0.00 | 0.03 | 0.00 | 20.78 |
| CU | ... | 0.73 | 0.31 | 0.21 | 0.65 | 2.14 | 0.07 | 0.41 | 0.60 | 2.20 |
| 5 | 3:12:57 PM | 4.26 | 82.87 | 151.24 | 130.93 | 5095.2 | 6.61 | 14.90 | 1.06 | 2137.8 |
| 4 | 3:11:32 PM | 4.24 | 82.51 | 151.82 | 132.95 | 5077.0 | 6.62 | 15.00 | 1.05 | 2166.5 |
| 3 | 3:10:06 PM | 4.21 | 82.65 | 151.37 | 132.96 | 5009.8 | 6.61 | 14.94 | 1.05 | 2138.0 |
| 2 | 3:08:49 PM | 4.27 | 82.35 | 151.46 | 131.80 | 4907.2 | 6.61 | 14.99 | 1.06 | 2074.1 |
| 1 | 3:06:13 PM | 4.29 | 82.21 | 151.99 | 132.28 | 4849.5 | 6.62 | 15.06 | 1.05 | 2058.0 |

Summary Statistics

FIG. 10c

| FIG.12A |
|---------|
| FIG.12B |

| RESULTS | VALUE | UNITS | μ±4SD | DATE |
|---|---|---|---|---|
| SPHERING PRESSURE | 85.02 | mOsm/Kg | 143.70 | 6/4/93 |
| Cp net | 3.48 | ml/m^2 | 3.10 | 6/4/93 |
| S.I. | 14.5 | ... | 17.50 | 6/4/93 |
| IsoV | 66.42 | fl | 91.00 | 6/4/93 |
| SphV | 96.46 | fl | 160.00 | 6/4/93 |

CELL IMAGE

CELL BY CELL ANALYSIS

RANGE: 330.00 TO 52.80 mOsm

| FREQUENCY DISTRIBUTIONS | | | | | | |
|---|---|---|---|---|---|---|
| DIST: | MEAN | SD | cv | skew | kurtosis | n |
| ISOTONIC | 16.45 | 7.02 | 43 | 4.0 | 39.9 | 43121 |
| SPHERICAL | 24.39 | 9.76 | 40 | 1.0 | 1.9 | 2598 |
| GHOST | 19.54 | 6.96 | 36 | 1.1 | 1.5 | 1276 |

| mOsm | HCT | P.C.V. TRUE VOL (ft) (HAEMOLYSIS ADJ.) | SENSOR mVolts (isc) | Kv SENSOR MV→VOL FIXED CORRECTION OF 0.0980 | Kshape PCV/SENSOR VOL | Kshape (kα=0.7518) | SENSOR VOL | Kshape ERROR V. |
|---|---|---|---|---|---|---|---|---|
| 290 | 38.2 | 92.0 | 670 | 65.7 | 1.40 | 1.40 | 91.93 | 1.00 |
| 258 | 41.2 | 98.6 | 678 | 66.4 | 1.48 | 1.40 | 92.75 | 0.94 |
| 226 | 44.5 | 105.9 | 756 | 74.1 | 1.43 | 1.35 | 100.38 | 0.95 |
| 193 | 49.6 | 116.6 | 933 | 91.4 | 1.28 | 1.26 | 115.39 | 0.99 |
| 177 | 52.2 | 122.3 | 1036 | 101.5 | 1.20 | 1.21 | 122.64 | 1.00 |
| 168 | 55.2 | 129.7 | 1106 | 108.4 | 1.20 | 1.17 | 126.94 | 0.98 |
| 161 | 58 | 136.3 | 1221 | 119.7 | 1.14 | 1.11 | 132.91 | 0.98 |
| 153 | 62 | 146.1 | 1349 | 132.2 | 1.11 | 1.04 | 137.96 | 0.94 |
| 145 | 61.5 | 147.8 | 1432 | 140.3 | 1.05 | 1.00 | 140.34 | 0.95 |
| 137 | 53 | 151.9 | 1380 | 135.2 | 1.12 | 1.03 | 138.93 | 0.91 |
| 129 | 31 | 144.5 | 1167 | 114.4 | 1.26 | 1.14 | 130.28 | 0.90 |
| 121 | 9.2 | 104.3 | 1052 | 103.1 | 1.01 | 1.20 | 123.66 | 1.19 |

TABLE 1

METHOD FOR TESTING A CELL SAMPLE

TECHNICAL FIELD

This invention relates to a method for testing a cell sample or a fluid sample.

Many types of cells as well as artificial cells may be tested according to the method of the present invention, although the test is especially suitable for testing red and white blood cells.

BACKGROUND ART

It is well known that certain diseases give rise to changes in the condition of blood and especially of the red blood cells. Blood characteristics such as red blood cell count, mean cell volume, haemoglobin content and haematocrits are commonly used in the diagnosis of disease.

The measurement of cell volume is one of the most informative investigations in clinical medicine. Cell size is an important indicator of pathology and in conjunction with haemoglobin, forms the basic classification of anemias. It is the basis of the differentiation of white blood cells and leukaemias, the assessment of prognosis in scores of diseases and is an invaluable screening device for the thalassaemias, the most common genetic disease in the world.

Existing methodology achieves good cell size measurements in the majority of patients, failing only in those whose red cell shape differs significantly from normal and in patients with abnormal serum osmolality. As cell shape is normally distributed, 4.56% of the population have red cells that deviate from normal cell shape by more than two standard deviations. These abnormal samples are over represented in hospitals because the deviations are associated with illness more often than those within normal limits. Consequently, clinical laboratories generate incorrect cell volume values in at least 4.56% of reported results, representing about 100,000 incorrect cell volume measurements in the United States each day. In the majority of patients, these results do not cause significant problems but occasionally the erroneous measurements result in misdiagnosis and patient's death. However, this error is rarely recognised because existing automated methods cannot detect it.

A normal human blood sample is isotonic with a solution having an osmolality of about 290 mosm $Kg^{-1}$, and at this osmolality the average red blood cell in the average individual will have a biconcave shape. It is well known that reducing the osmolality of the solution surrounding a red blood cell below a critical level will cause that cell to swell, then rupture, forming a ghost cell which slowly releases its contents, almost entirely haemoglobin, into the surrounding medium. This process, called haemolysis, can be induced using water (osmotically) or by detergents, venoms or other chemicals, thermal, mechanical or electrical agents. Tests to determine cell volume are typically carried out at isotonic osmolality.

Automated measures of cells depend upon both size and shape of the cells being tested. Since existing instruments cannot determine cell shape, instruments such as the particle counter sold under the Trade Mark Coulter Counter by Coulter Electronics Inc., compensate in the calculation of isotonic cell volume with a term that is a fixed average estimate that is in error whenever the cell shape in a sample deviates from the normal population. It is these abnormal samples that indicate pathology where accuracy is most needed that the method most often fails.

In order to estimate the size and the count of the number and properties of red blood cells in a sample, there are several commercial particle counters available which may be used. These particle counters act either by measuring the electrical or optical properties of a stream of cells that pass along a narrow tube. The property measured is usually the current flowing through the suspension in the tube or the electrical field within the tube. The signal generated depends upon several factors including cell size, cell shape and the properties of the cell membrane the difference in the electrical property of the cell and the suspending medium.

DISCLOSURE OF INVENTION

According to a first aspect of the present invention, there is provided a new method in which a sample of cells suspended in a liquid medium, wherein the cells have at least one measurable property distinct from that of the liquid medium, is subjected to analysis by a method including the steps of:

(a) passing a first aliquot of the sample cell suspension through a sensor, (b) measuring said at least one property of the cell suspension, (c) recording the measurement of said property for the first aliquot of cells, (d) subjecting the first or at least one other aliquot of the sample cell suspension to an alteration in at least one parameter of the cell environment which has the potential to alter the shape of the cells to a known or identifiable extent to create an altered cell suspension, (e) passing said altered cell suspension through a sensor, (f) measuring said at least one property of the altered cell suspension, (g) recording the measurement of said at least one property for said altered suspension, (h) comparing the data from steps (c) and (g) and determining a shape compensation factor to be applied to the measurement of said at least one property of the first aliquot of cells in step (c) in the calculation of a cell parameter to take account of a variation in shape between the first aliquot of cells in step (c) and said altered cell suspension in step (g).

In the present invention, a cell parameter, for example cell volume, is determined by subjecting one or more aliquots of a sample cell suspension to one or more alterations of at least one parameter of the cell environment to identify a point at which the cells achieve a particular shape to obtain a sample specific shape compensation factor.

All existing automated methods include a fixed shape correction in the treatment of sensor readings taken from a single cell suspension in which the cell environment is not altered during the course of the test, which compensates for the deviation of the cells from spherical shape particles commonly used to calibrate the instruments. However, in a calculation of cell volume, as the cell shape is unknown, a fixed correction of approximately 1.5 is entered into the calculation on the assumption that a sample cell has the shape of a biconcave disc. This correction is correct for the average cell in the average person at isotonic osmolality, but it is incorrect for many categories of illness where the assumed fixed correction may induce an error of up to 60% in the estimate of cell volume. In the method of the present invention, an estimate is made of the in vivo cell shape so that a true estimate of cell volume or other cell parameter at all shapes is obtained. In the preferred embodiment of the present invention, a shape correction function is determined which is used to generate a shape correction factor which is a measure of the shape of the cell specific for that cell sample. The value of the shape correction factor generated by this function then replaces the conventional fixed shape correction of 1.5 to obtain a true measure of cell volume and other cell parameters.

According to a second aspect of the present invention, an apparatus for testing a sample cell suspension in a liquid medium in accordance with the method of the first aspect of the present invention comprises data processing means programmed to compare data from said steps (c) and (g) to determine a shape compensation factor to be applied to the measurement of said at least one property of the first aliquot of cells in the calculation of a cell parameter to take account of a variation in shape between the first aliquot of cells and said altered cell suspension.

Preferably, the data processing means comprises the internal microprocessor of a personal computer.

Preferably, the property of the cells which differs from the liquid medium is one which is directly related to the volume of the cell. Such a property is electrical resistance or impedance, and this is measured as in the normal Coulter Counter by determining the flow of electrical current through the cell suspension as it passes through a sensing zone of the sensor. The sensing zone is usually a channel or aperture through which the cell suspension is caused to flow. Any type of sensor may be used provided that the sensor produces a signal which is proportional to the cell size. Such sensor types may depend upon voltage, current, RF, NMR, optical, acoustic or magnetic properties. Most preferably, the sensor is substantially as described in our co-pending International application also filed this day WO 97/24600.

Although the method is usually carried out on blood cells, for instance white or, usually, red blood cells, it may also be used to investigate other cell suspensions, which may be plant or animal cells or micro-organism cells, for instance, bacterial cells.

The environmental parameter which is changed in the method may be any change which will result in a measurable parameter of the cells being altered. The method is of most value where the change in environmental parameter changes the size, shape, or other anatomical property of the cell. The method is of particular value in detecting a change in the volume of cells as a result of a change of osmolality of the surrounding medium. Preferably therefore, the environmental parameter change is an alteration, usually a reduction, in osmolality. Typically the environment of the first aliquot is isotonic, and thus the environment of the altered suspension in step (g) is rendered hypotonic, for instance by diluting a portion of isotonic sample suspension with a hypotonic diluent.

The method of the present invention, as well as being applicable to cells, as described above, may also be applicable to other natural and synthetic vesicles which comprise a membrane surrounding an interior space, the shape or size or deformability of which may be altered by altering an environmental parameter. Such vesicles may be useful as membrane models, for instance, or as drug delivery devices or as devices for storing and/or stabilising other active ingredients or to contain haemoglobin in blood substitutes.

In the method, the time between the initiation of the alteration of the environment to the passage of the cells through the sensing zone may vary but preferably is less than 1 minute, more preferably less than 10 seconds. The time is generally controlled in the method and preferably it is kept constant. If it changes, then time may be a further factor which is taken into account in the calculation step of step (h).

Although it is possible for the method of the invention to comprise merely of the treatment of two aliquots of the sample cell suspension, more usually the method includes the steps of subjecting another aliquot of sample cell suspension to a second alteration in at least one parameter of the cell environment passing said altered aliquot through the sensor, recording the change in said property of the cell suspension under the altered environment as each of a number of cells of the aliquot passes through the sensor, recording all the concomitant properties of the environment together with the said change on a cell-by-cell basis, and comparing the data from previous step (c) and the preceding step as a function of the extent of said second alteration of environmental parameter. Usually there are many further aliquots treated in a similar way. The greater the number of aliquots tested, the greater the potential accuracy, precision and resolution of the results which are obtained. It is also possible to subject a only single aliquot of sample suspension to a series of such alterations in at least one parameter of the cell environment.

In its simplest form, the test is dependent upon two sensor measurements, one of which is at a maximum, or near to it. However, the environment required to induce a cell to reach a maximum size can be entirely unknown. Furthermore, the environmental changes can be sequential, non-sequential, non-sequential, random, continuous or discontinuous, provided that the maximum achievable cell size is recorded. One convenient way of ensuring this is to test the cell in a continuously changing environment so that all possible cell sizes are recorded, including the maximum.

The second alteration in the cell environment is usually of the same type as the first alteration. It may even be of the same extent as the first alteration, but the time between initiation of the alteration and passage of the cells through the sensing zone may be different, thereby monitoring the rate of change in the cells properties when subjected to a particular change in environmental parameter. This technique may also be used to monitor cells which have been in storage for several years.

In another embodiment the second alteration in environmental parameter is of the same type as the first alteration, but has a different extent. In such a case, it is preferred for the time between initiation of the alteration and passage of the cells through the sensing zone to be the same for each aliquot of the cell suspension. Preferably, in this embodiment of the method second and subsequent aliquots of cell suspension are subjected to successively increasing extents of alteration of the environmental parameter such that the change of said property produces a maximum and then decreases as the extent of alteration of environmental parameter is increased. In the preferred embodiment in which the property of the cell suspension which is monitored is directly related to the volume of the cells, and where the alteration of environmental parameter for the second and subsequent aliquots results in a volume increase of the cells, preferably, the environmental change is varied until the cell volume passes a maximum.

Since the preferred application of the method of the present invention is to analyse red blood cells, the following discussion is based mainly on the study of such cells. It will be realised, however, that the method is, as mentioned above, applicable to other cell types and to determine other information concerning an organism from a study of such cell types.

In current practice, cell shape, particularly red blood cell shape, is not estimated by any automated method. The present invention enables the user to determine cell shape and derive other data, such as cell volume, surface area, surface area to volume ratio, sphericity index, cell thickness, and surface area per millilitre. Aside from research and experimental laboratories, none of these measurements are currently available in any clinical laboratory and hitherto, none could be completed within 60 seconds. In particular, the preferred method where the sample cell suspension is subjected to a concentration gradient, enables the automatic detection or a user to detect accurately when the cells adopt a substantially spherical shape immediately before lysis.

The commercially available Coulter Counter particle counter instrument produces a signal in proportion to the volume of particles which pass through a sensing zone, typically a voltage pulse for each particle. The size of the signal is calibrated against spherical latex particles of known volume to produce a conversion factor to convert a measured signal, typically voltage, into a particle volume, typically femtolitres. When using particle counters of this type to measure the size of particles that are not spheres, as is typical in biological samples such as platelets, fibroblasts or red blood cells which have the shape of a disc, a fixed shape correction factor is used in addition to the conversion factor. This fixed shape correction, based on theoretical and empirical data, is designed to produce a correct volume estimate when measuring particles that are not spherical as the size of the voltage pulses are not solely related to cell volume. For instance, normal red blood cells produce sensor pulses which are too small by a factor of around 1.5 when measured on these instruments and therefore a fixed correction of 1.5 is entered into the calculation of cell volume to produce the correct valve.

In the preferred method of the present invention, this fixed shape correction factor is replaced with a sample specific shape correction factor $f(K_{shape})$, generated from a shape correction function. The shape correction function is continuous for all cell shapes and ranges in value from 1.0 for spherical cells to infinity for a perfectly flat cell. The shape correction function increases the accuracy with which cell parameters which depend on anatomical measurement, such as cell volume, can be determined.

In the preferred method where the environmental parameter change is a reduction in osmolality, the following general function describes a shape correction factor based on any two sensor readings ie. measured voltages:

$f(K_{shape})=f(SR1, SR2)$ where SR1 is a sensor reading (measured voltage) at a known shape, typically spherical, and SR2 is a sensor reading at an osmolality of interest, typically isotonic. In the preferred method, the sensor reading is one of voltage amplitude.

Analysis has shown that this is a linear function and that:

$$f(K_{shape}) = 1 + \left[\frac{(SR1-SR2)}{(SR1)}\right] \times K_a$$

where $K_a$ is an apparatus dependent constant.

Preferably, the shape correction factor a blood cell is determined by comparing the measured voltage (SR1) with the measured (SR2) voltage of cells of the same blood sample at some known or identifiable shape, most conveniently cells which have adopted a spherical shape.

According to a third aspect of the present invention there is provided a new method in which a sample of cells suspended in a liquid medium, wherein the cells have at least one measurable property distinct from that of the liquid medium, is subjected to analysis by a method including the steps:

(a) passing a first aliquot of the sample cell suspension through a sensor, (b) measuring said at least one property of the cell suspension as each of a number of cells of the first aliquot passes through the sensor, (c) recording the measurement of said property for the first aliquot of cells on a cell-by-cell basis, (d) subjecting the first or at least one other aliquot of the sample cell suspension to an alteration in at least one parameter of the cell environment which has the potential to alter the said at least one property of the cells to create an altered cell suspension, (e) passing said altered cell suspension through a sensor, (f) measuring said at least one property of the altered cell suspension as each of a number of cells of the altered cell suspension passes through the sensor, (g) recording the measurement of said at least one property for the altered cell suspension on a cell-by-cell basis, (h) comparing the data from steps (c) and (g) as a function of the extent of said alteration of said parameter of the cell environment and frequency distribution of said at least one property.

By carrying out the method of the invention, and in particular by recording the property change data for the cells on a cell-by-cell basis, the data can be subsequently treated so as to identify sub-populations of cells within the sample which respond differently to one another under the imposition of the environmental parameter alteration.

The present invention provides a method for testing blood samples which enables data to be obtained on a cell-by-cell basis. By using the data on a cell-by-cell basis, it enables new parameters to be measured and to obtain information on the distribution of cells of different sizes among a population and reveal sub-populations of cells based on their anatomical and physiological properties.

A measure of reproducibility is the standard deviation of the observations made. An aspect of the present invention is to provide improvements in which the standard deviation of the results obtained is reduced to ensure clinical utility.

According to a fourth aspect of the present invention, an apparatus for testing a sample cell suspension in a liquid medium in accordance with the method of the third aspect of the present invention comprises data processing means programmed to compare data from said steps (c) and (g) as a function of the extent of said alteration of said parameter of the cell environment and frequency distribution of said at least one property.

Other environmental parameter changes which may be investigated include changes in pH, changes in temperature, pressure, ionophores, changes by contact with lytic agents, for instance toxins, cell membrane pore blocking agents or any combinations of these parameters. For instance, it may be useful to determine the effectiveness of lytic agents and/or pore blockers to change the amount or rate of cell volume change on a change in environmental parameters such as osmolality, pH or temperature. Furthermore the effects of two or more agents which affect transport of components in or out of cells on one another may be determined by this technique. It is also possible to subject the cell suspension to a change in shear stress during the passage of the cell suspension through the sensing zone by changing the flow rate through the sensor, without changing any of the other environmental parameters or in conjunction with a change in other environmental parameters. A change in the shear stress may affect the shape of the cell and thus the electrical, optical or other property which is measured by the sensor. Monitoring such a change in the deformation of cells may be of value. In particular, it may be of value to monitor the change in deformability upon changes imposed by disease or, artificially by changing other environmental parameters, such as chemical components of the suspending medium, pH, temperature or osmolality.

Preferably, the data processing means comprises the internal microprocessor of a personal computer.

When full data are available on the distribution of cell size in a particular population of cells subjected to haemolytic shock in a wide range of hypotonic solutions, at osmolalities just below the critical osmolality causing lysis, a gap in the populations is visible. On a 3-D plot or an alternative way of representing the data such as a contour map, the ghost cells are clearly visible and the unruptured cells are clearly identifiable, but between them there is a region defined by, for example, osmolality and cell size where the cells are widely distributed. The existence of this phenomenon, which we have termed "ghost gap", has not previously been recognised, and it has been discovered that the nature of this phenomenon varies with species and between healthy and diseased individuals of particular species. It is a measure of the degree of anisocytosis (size heterogeneity) and can be used in the measurement of the degree of poikilocytosis (shape heterogeneity) of the cell population, which is often used as the basis for classifying all anaemia.

The measurements of the cell parameter changes may be stored and retrieved as voltage pulses and they may be displayed as individual dots on a display of voltage against the osmolality of the solution causing the parameter change. When observations are made using a suspension at a single tonicity, the resulting plot shows the frequency distribution of voltage by the intensity of the dots representing cells of the same volume.

The number of blood cells within each aliquot which are counted is typically at least 1000 and the cell-by-cell data is then used to produce an exact frequency distribution of size. Suitably this density can be made -more visible by using different colours to give a three dimensional effect, similar to that seen in radar rainfall pictures used in weather forecasting. Alternatively, for a single solution of any tonicity, the measured parameter change could be displayed against the number of individual cells showing the same change. In this way a distribution of cell volume or voltage in a particular tonicity of given osmolality can be obtained.

The method of the invention may be further improved by, instead of subjecting portions of a sample each to one of a series of hypotonic solutions of different osmolalities to form the individual aliquots, the sample is fed continuously into a solution, the osmolality of which is changed continuously to produce a continuous gradient of aliquots for passage through the sensing zone. Preferably, identical portions of the sample under test are subjected to solutions of each osmolality throughout the range under test after the same time from imposition of the environmental parameter change to the time of passage through the sensing zone. This technique ensures that the cells are subjected to each concentration which cause critical changes in that particular sample. Further, an effect of feeding the sample under test into a continuously changing osmolality gradient, is to obtain measurements which are equivalent to treating one particular cell sample with that continuously changing gradient. This technique is the subject of our co-pending International patent application also filed this day WO 97/24529.

Further, in the present invention, it is possible to examine a particular blood sample at various intervals of time and compare the sets of results to reveal dynamic changes in cell function.

These dynamic changes have revealed that cells slowly decrease their ability to function over time, but they also change in unexpected ways. The size and shape of the cells in a blood sample change in a complex, non-linear but repeatable way, repeating some of the characteristic patterns of change over the course of days and on successive testing. The patterns, emerging over time, show similarity among like samples and often show a characteristic wave motion. The pattern of change may vary between individuals reflecting the health of the individual, or the pattern may vary within a sample. Thus a sample that is homogeneous when first tested may split into two or several sub-populations which change with time and their existence can be detected by subjecting the sample to a wide range of different tonicities and recording the cell size in the way described.

If the entire series of steps are repeated at timed intervals on further aliquots of the original sample and the resulting property change is plotted against osmolality, time and frequency distribution, a four-dimensional display, is obtained which may be likened to a changing weather map. The rate of change of the property in relation to the time taken to perform each test must be such that any changes which occur during the test must not substantially affect the results.

It is this moving three-dimensional display (motion in time being the fourth dimension), which provides a pattern characteristic of a particular blood sample. The pattern includes the density of particular cell voltages and thereby sizes, the shape of the area representing ghost cells and particularly the shape and location of a gap between the whole cells and the ghost cells. This pattern and its variation with species and the health of individuals within a species provides a characteristic which may be used in clinical diagnosis and other disciplines. Cell shape is one property that is the basis of this dancing or changing display. For the first few hours the cell becomes increasingly spherical in the original sample, it then becomes flatter for several hours, then more spherical again reaches a limit and then becomes thinner and finally may swell again. This set of curious changes in shape also occurs within a blood clot and is the basis of the hitherto puzzling changes in opacity of the brain after a stroke observed by NMR, (1) Gomori J. M., Grossman R. I. et al, Radiology 157, 1985, p. 87 to 93; (2) Bydder G. M., Pennock J. M., Porteous R. et al, 1988, Neuroradiology 30, p. 367 to 371; (3) Alanen A., Kormano M. 1985, J. Ultrasound Med 4., 421 to 425. By using the method of the present invention it has been determined that the rate at which observed changes take place either within a clot or in a whole blood sample are influenced by pH, temperature and available energy.

The 3D pattern enables identification of the precise osmolality at which particular cells reach their maximum volume, i.e. when they become spheres. With appropriate calibration, and using the magnitude of the voltage pulse, it is possible to define precisely and accurately the actual volume of such cells. By causing cells to pass through their maximum and differentiating, identification of the point of lysis ie sphered cells is obtained to the nearest $\frac{1}{10}$ mosm $Kg^{-1}$. When the mean cell volume is required, the data is taken from the voltages and thereby the volume at isotonic osmolality corrected for the proportion of cells that are more leptocytotic or spherocytic than normal and the degree of that deviation. When individual cell volumes are required they are obtained directly from the observed voltage pulse or from the frequency distribution data with dispersion statistics or its graphical representation.

In a preferred form of the invention, when the measurements of a blood sample are made against a continuous gradient of osmolality and the results displayed as a pattern or contour map of the individual cell measurements and showing the distribution of cells of different sizes by the density of the pattern, repeating this measurement at intervals of time and then examining each in time sequence reveals that a typical cell sample may contain sub-populations of cells which change with time in a different way from other cells in that sample. Examination of the patterns obtained at different points in time is preferably done by computer sequencing which gives the effect of the dynamic changes in the cells in the form of a moving picture. Using this technique, two or more cell sub-populations may be followed to determine the fate and the relative proportion of each population. This is useful as a means to monitor, for example the recovery of the bone marrow in an anaemia that is under treatment, a leukaemia that has received chemotherapy, a bone marrow transplant or as a means to study the storage lesion in stored blood.

According to a further feature of the invention there is provided a method for the diagnosis of abnormalities in a blood cell sample which comprises using the invention whereby the data retrieved on an individual cell basis, or a summary there of, from an experimental source is compared with data retrieved on an individual cell basis from a standard sample. It will be clear from the description given above that the data available from the improved method of the present invention provides a pattern and a method of calculating a number of individual blood cell parameters which are capable of comparison with standard samples. This comparison provides the basis for a wide range of clinical diagnosis. In particular, the pattern or contour map obtained by conducting measurements against a continuous gradient of osmolality provides a pattern capable of giving a great deal of diagnostic information and summaries of such data.

Attention is also drawn to the use of data obtained by measurements carried out at different timed intervals. By viewing the cell population at such timed interval and noting the changes in the pattern which take place, much valuable diagnostic information can be obtained by skilled persons. Again a great deal of work needs to be done to identify and correlate particular changes in this pattern with clinical conditions. However it is clear that the existence of this variation in pattern with time will prove to be a significant diagnostic tool.

The method of the invention may be used in medicine, for example in clinical diagnosis to detect the presence of disease, or to assess remission and prognosis of a diseased state, or in blood banks to assess the condition of stored blood. The invention will also have value in veterinary persons. Again a great deal of work needs to be done to identify and correlate particular changes in this pattern with clinical conditions. However it is clear that the existence of this variation in pattern with time will prove to be a significant diagnostic tool.

The method of the invention may be used in medicine, for example in clinical diagnosis to detect the presence of disease, or to assess remission and prognosis of a diseased state, or in blood banks to assess the condition of stored blood. The invention will also have value in veterinary medicine for diagnosis and in zoology as a guide to taxonomy.

This invention has the advantage of being able to detect subtle changes in red cell morphology, and in particular cell shape changes, long before the cell shows gross changes that may be detectable by existing methods. For example, gross changes in the red cell thickness which cannot be quantified but can usually be detected by light microscopy, can be quantified using the method of the invention. Further small changes in the red cell thickness cannot be detected or quantified by existing methods, but can be both detected and quantified using the method of the invention.

The invention has been shown to be useful in the clinical diagnosis of many conditions with thin cells and in particular:

Thin Cells or Leptocytes
1. Hereditary stomatocytosis
2. Mediterranean stomatocytosis
3. Cryohydrocytosis
4. Adenine deaminase hyperactivity
5. Obstructive liver disease
6. Rh null blood group This invention has been shown to be useful in the clinical diagnosis of spherocytic cells in a sample (ie. cell which have more of a spherical shape than is normal) can be an indication of one of the following:
1. ABO haemolytic disease
2. Hereditary spherocytosis
3. Immunohaemolytic anaemias (Coombs positive)
4. Transfusion reaction
5. Clostridia infections
6. Burns
7. Venoms from snakes, spiders or bees
8. Hypophosphotaemia
9. Hypersplenism
10. Pregnancy This list gives an indication of the clinical value of the present invention which is greatly enhanced once the changes can be quantified and the subtler changes are associated with disease. The ability to measure the degree of thickness or thinness of cells allows the possibility to study the progress of the disease and assess the value of treatment, especially at an early stage.

Other parameters identifiable by the method of the invention may be used to identify other species.

BRIEF DESCRIPTION OF DRAWINGS

The present invention will now be described in detail with reference to the accompanying drawings, in which:

DETAILED DESCRIPTION

Figure 1:
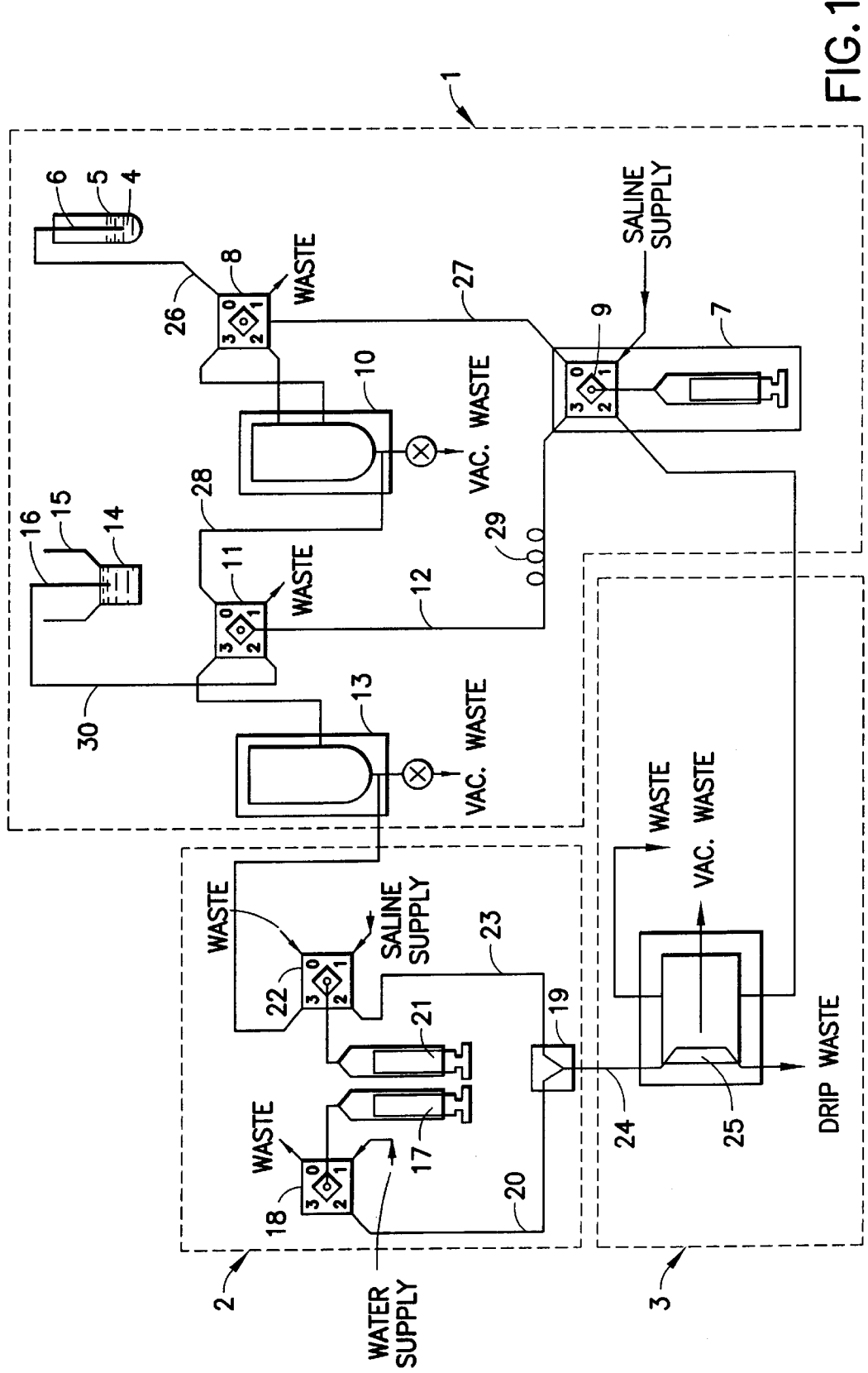
Figure 2:
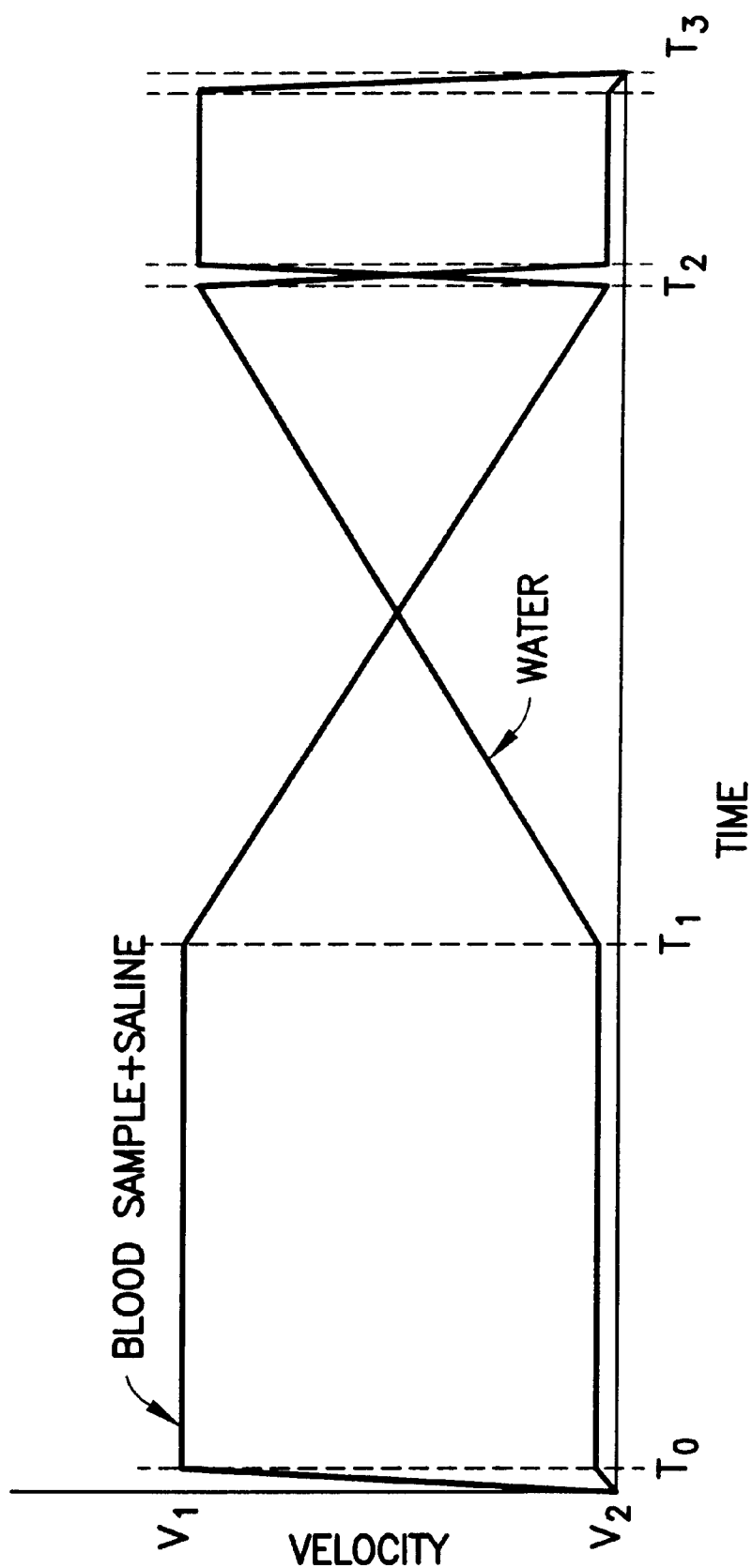
Figure 3:
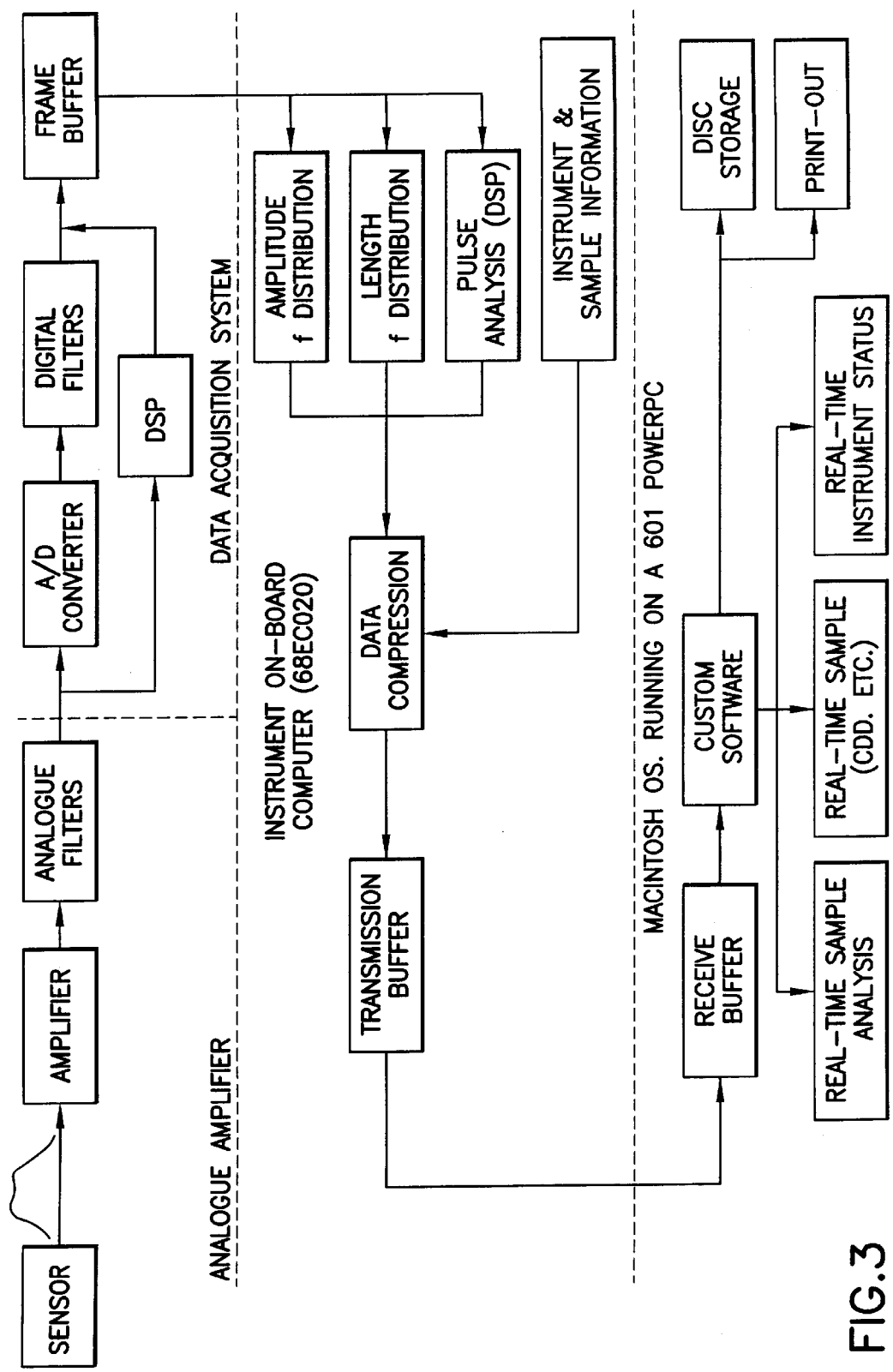
Figure 4:
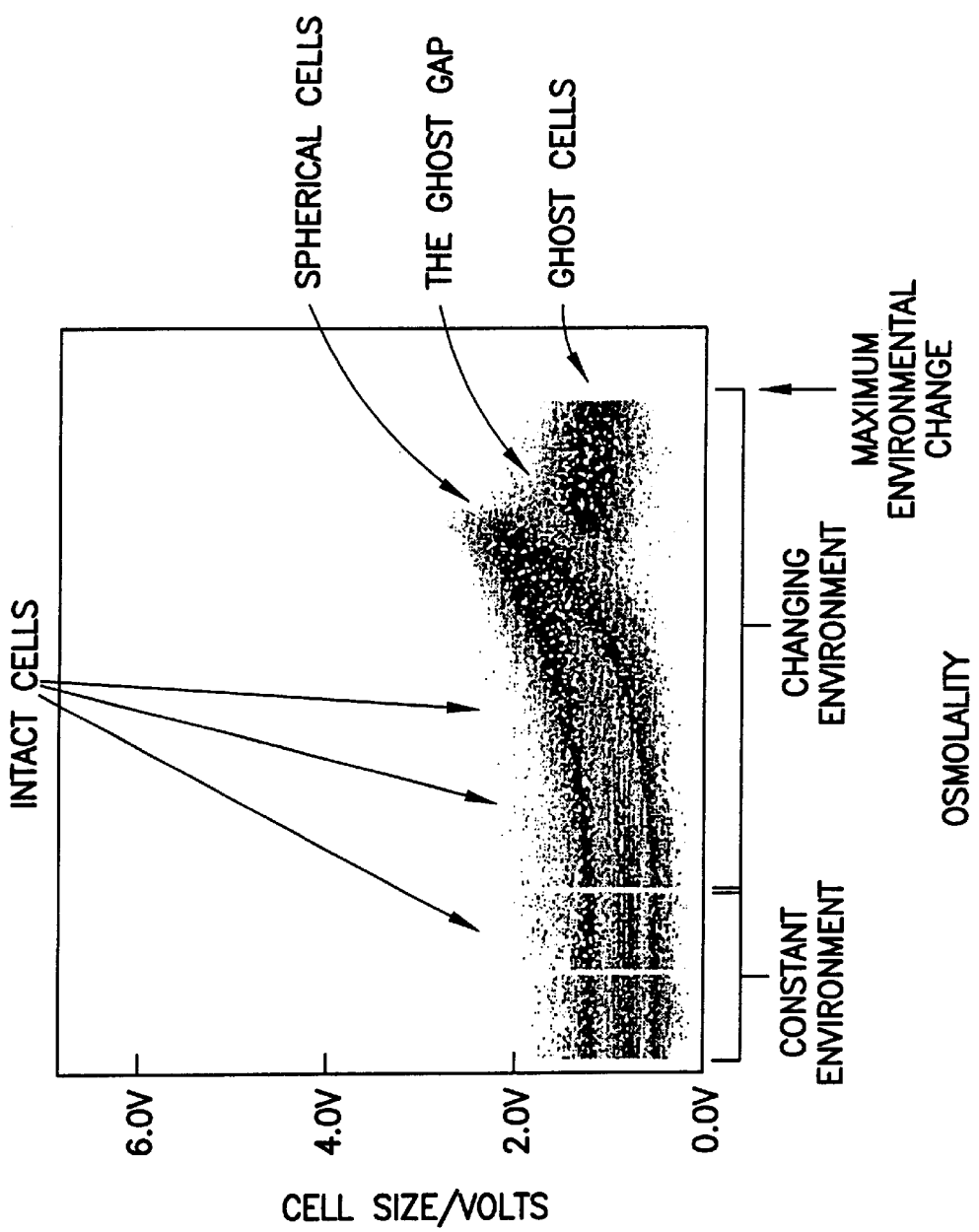
Figure 5:
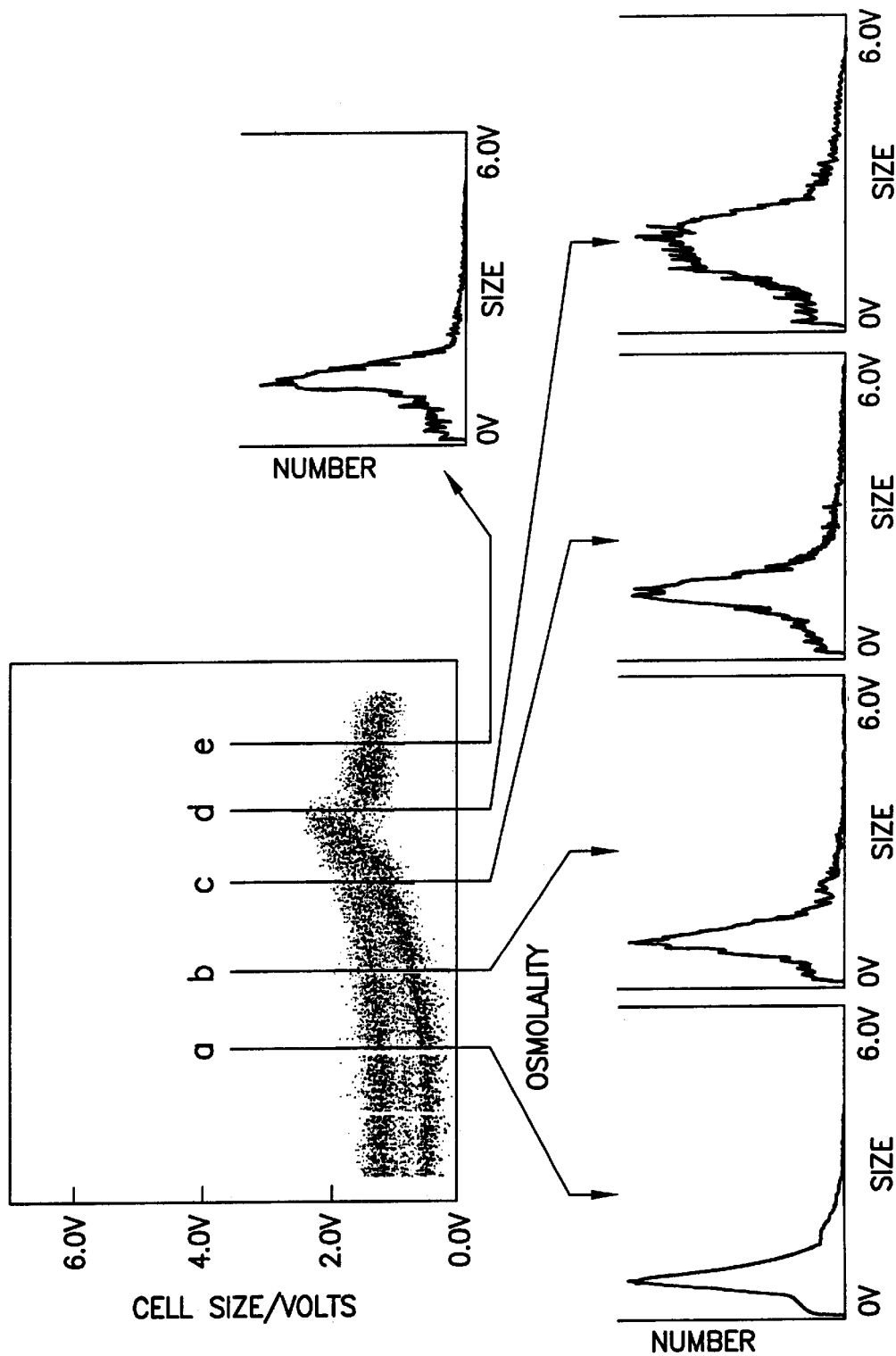
Figure 6:
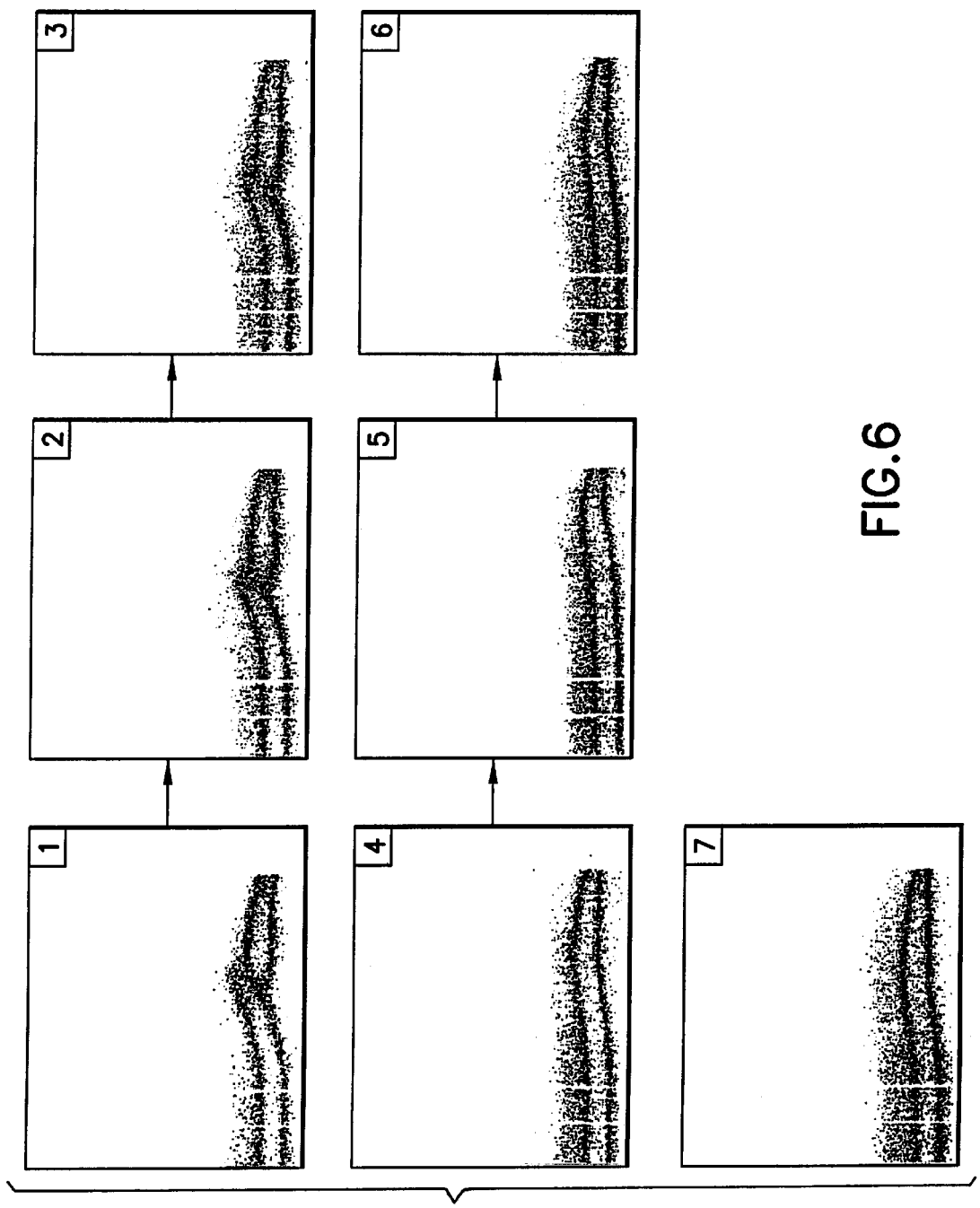
Figure 7:
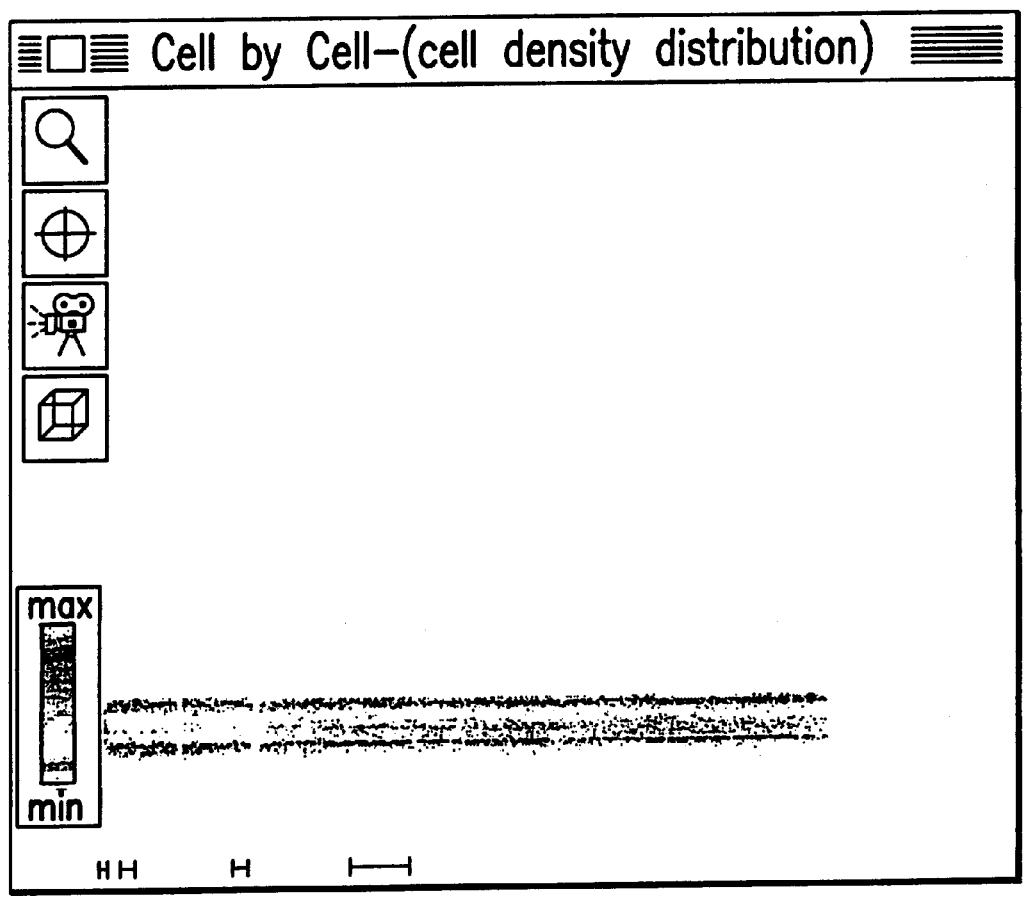
Figure 8:
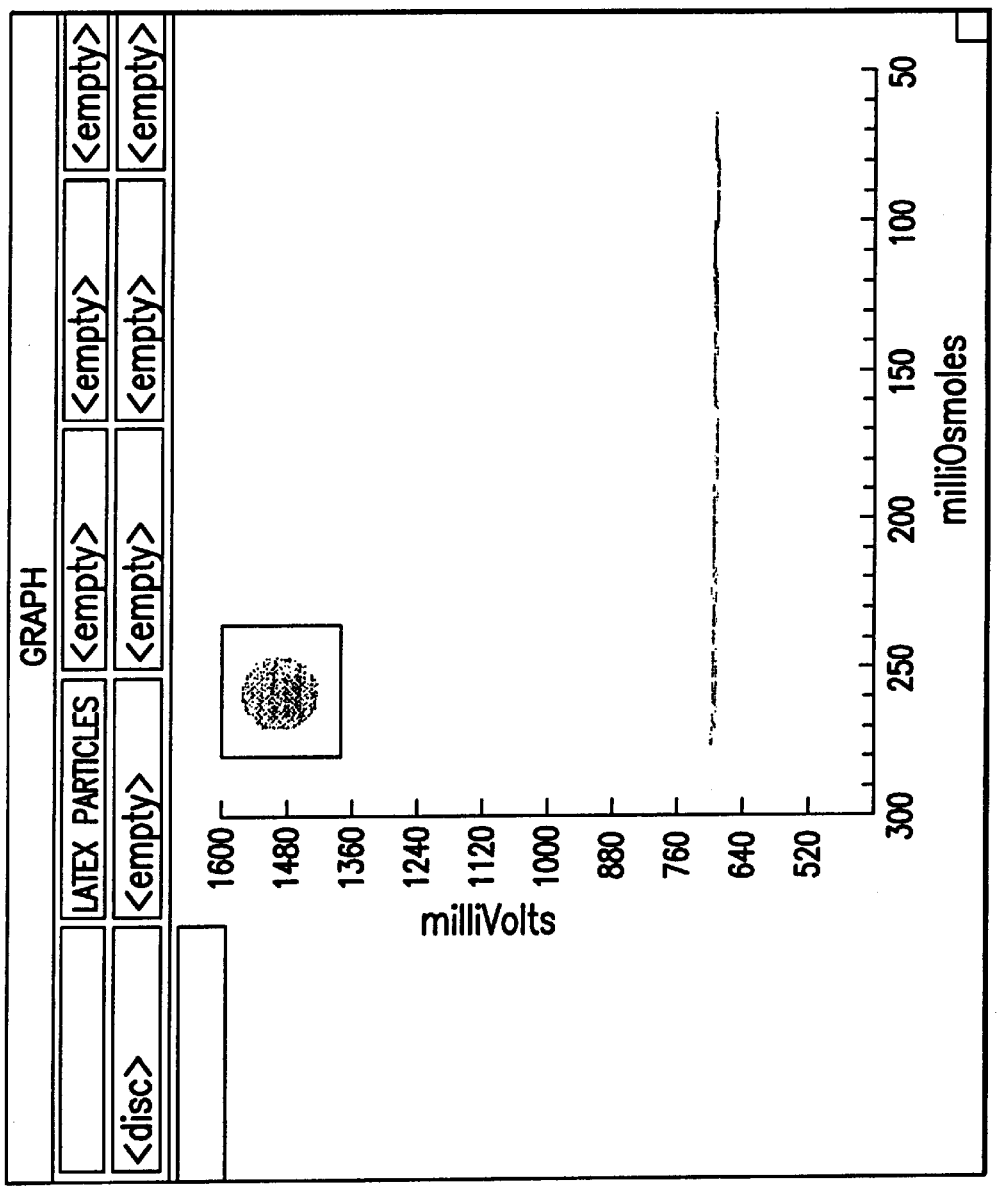
Figure 9:
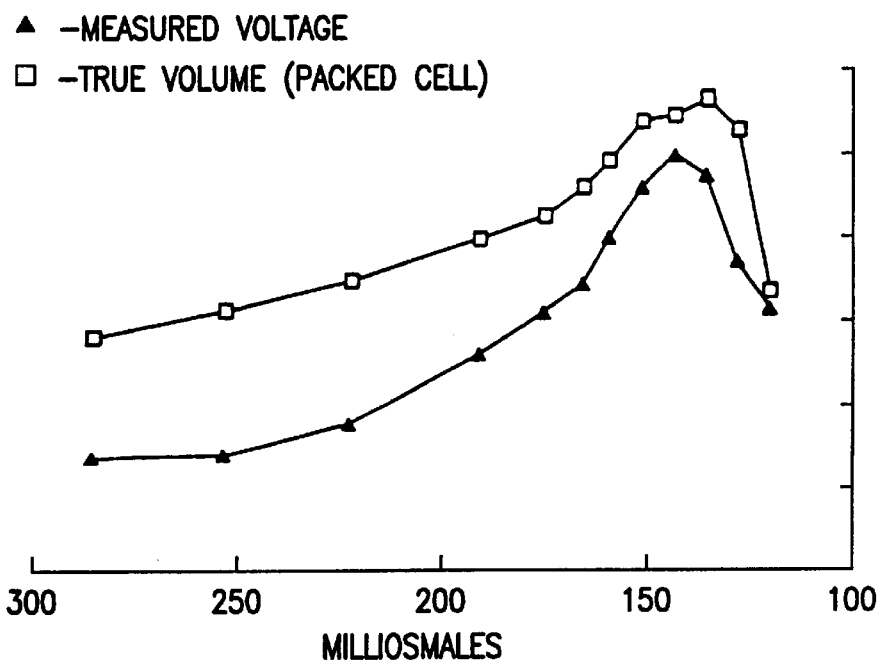
Figure 10A:
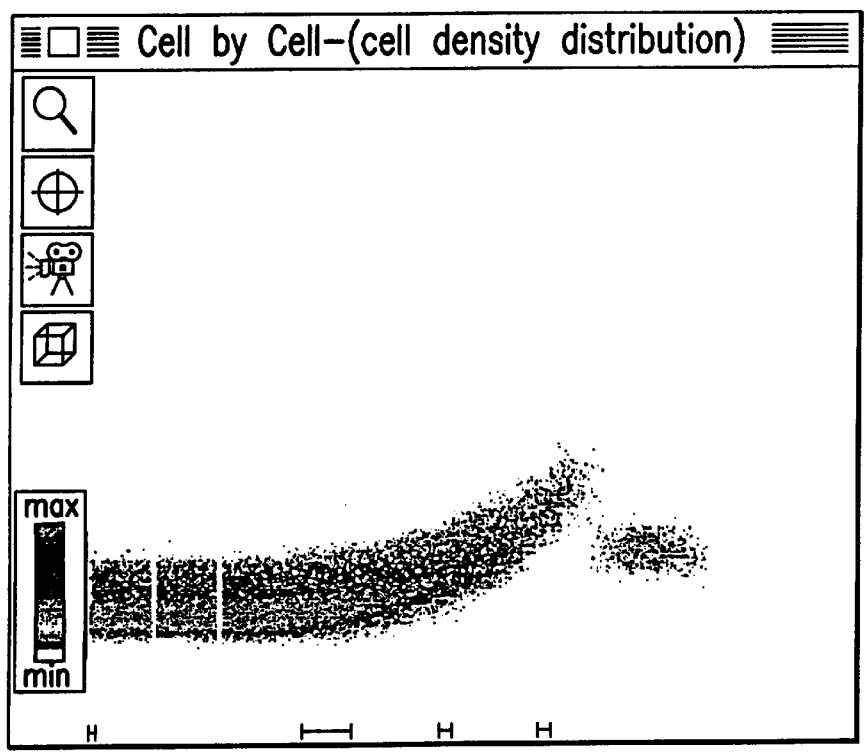
Figure 10B:
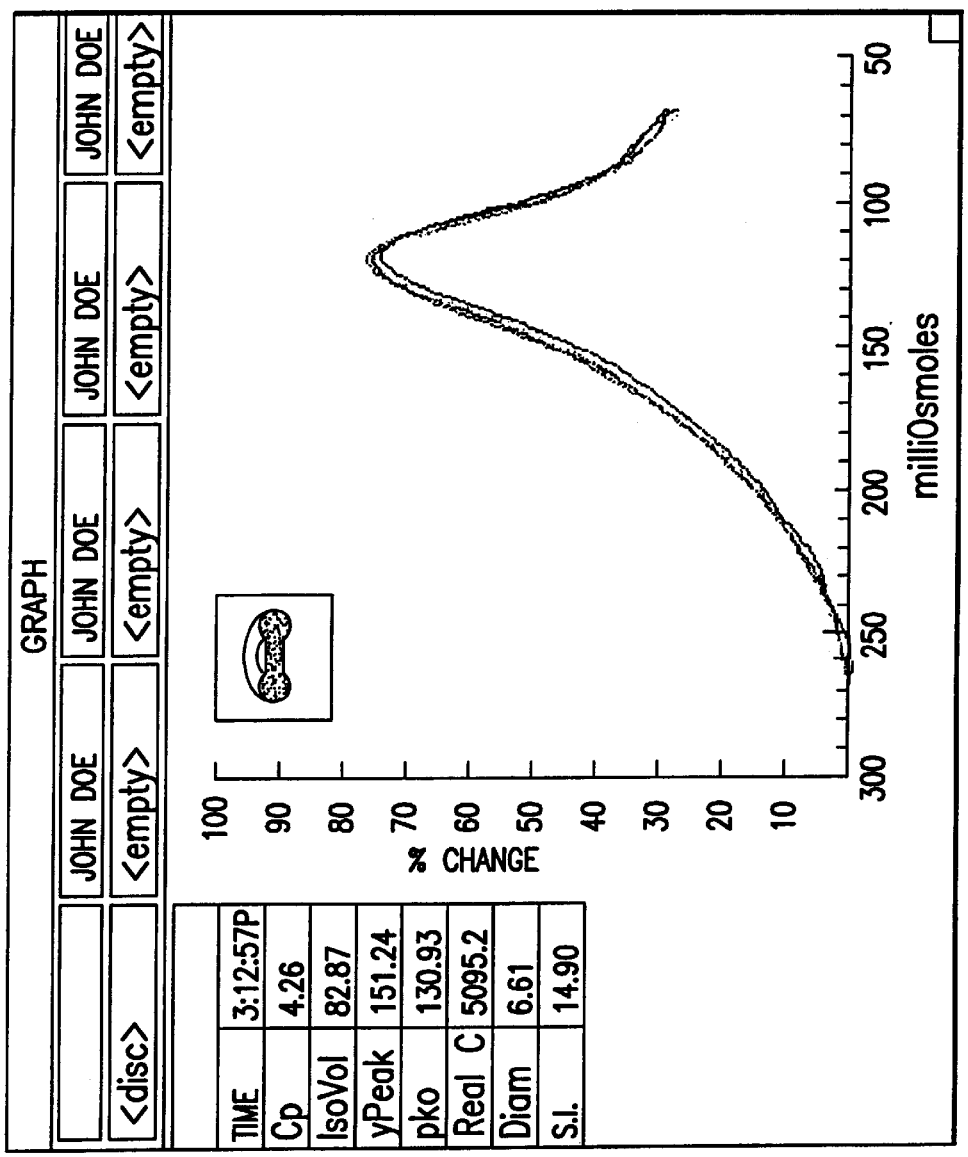
Figure 10D:
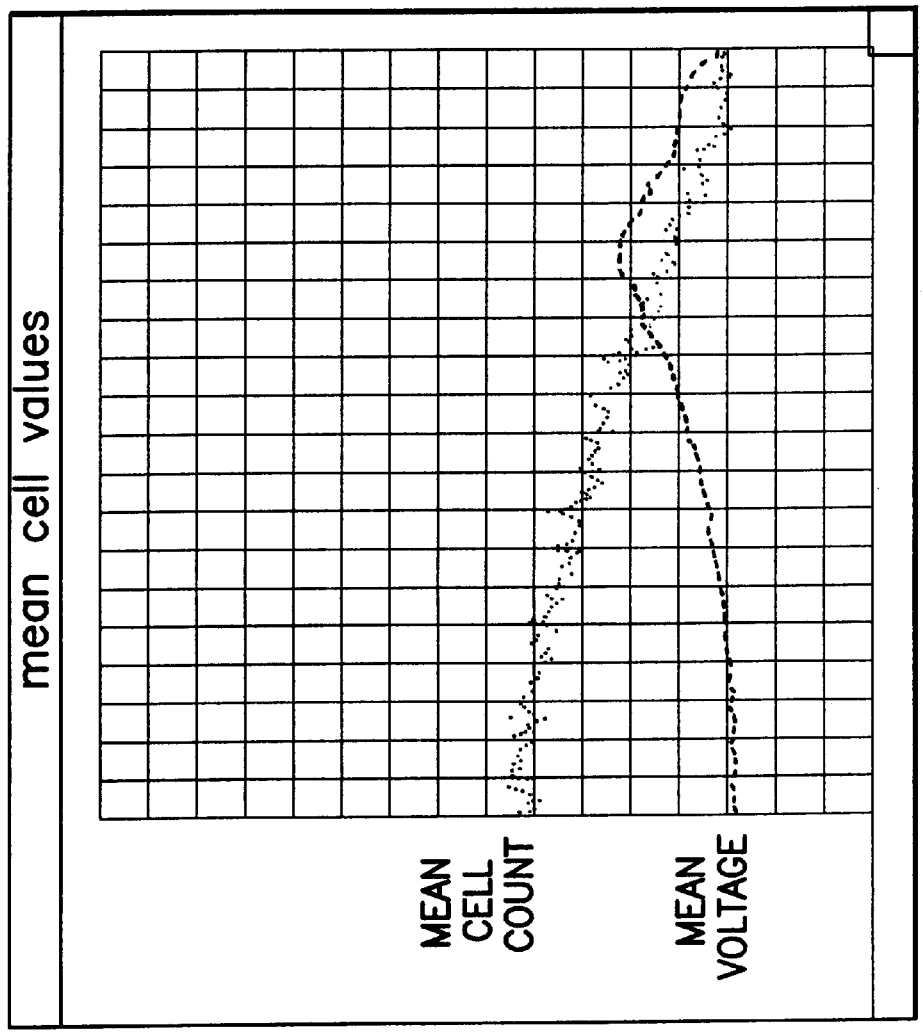
Figure 11:
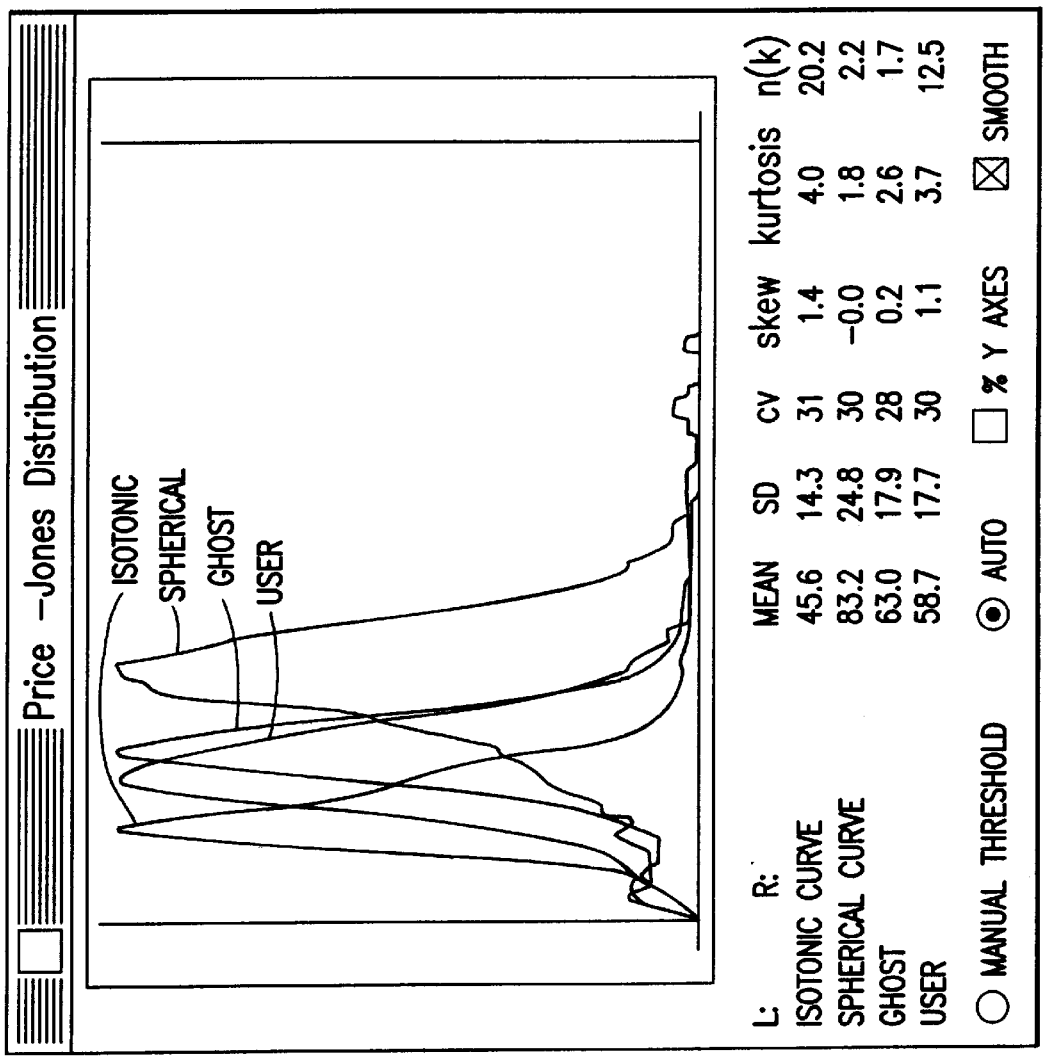
Figures 12, 12A:
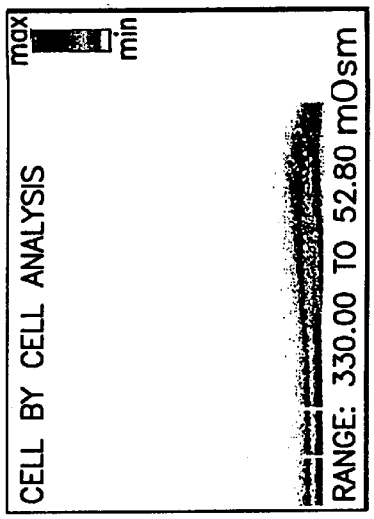
Figure 12B:
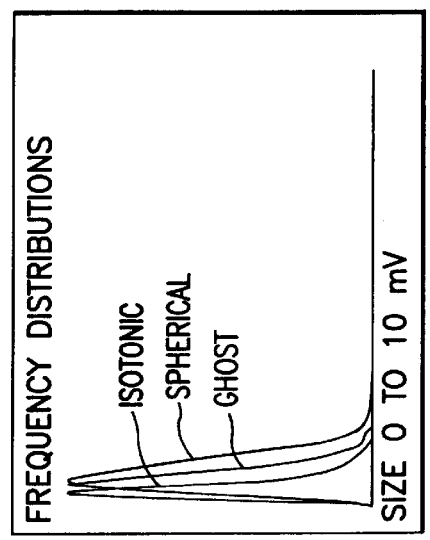

FIG. 1 shows schematically an instrument used to sample and test blood cells;

FIG. 2 shows velocity profiles for the discharge of fluids from fluid delivery syringes of a gradient generator section of the instrument of FIG. 1;

FIG. 3 shows a block diagram illustrating the data processing steps used in the instrument of FIG. 1;

FIG. 4 shows an example of a three-dimensional plot of osmolality against measured voltage for cells of a blood sample analyzed in accordance with the present invention;

FIG. 5 shows another example of a three-dimensional plot of osmolality against measured voltage which illustrates the frequency distribution of blood cells at intervals;

FIG. 6 shows a series of three-dimensional plots for a sample tested at hourly intervals;

FIGS. 7 and 8 show results for spherical latex particles as part of an instrument calibration routine;

FIG. 9 shows superimposed plots of osmolality (x-axis) against measured voltage and true volume, respectively;

FIGS. 10a to 10d show the results from the test of a healthy individual;

FIG. 11 shows Price-Jones curves of the results shown in FIGS. 10a to 10d; and,

FIG. 12 shows a three-dimensional frequency distribution plot and cell parameters for an abnormal individual.

FIG. 1 shows schematically the arrangement of a blood sampler for use in the method of the present invention. The blood sampler comprises a sample preparation section 1, a gradient generator section 2 and a sensor section 3.

A whole blood sample 4 contained in a sample container acts as a sample reservoir for a sample probe 6. The sample probe 6 is connected along PTFE fluid line 26 to a diluter pump 7 via multi-position distribution valve 8 and multi-position distribution valve 9. The diluter pump 7 draws saline solution from a reservoir (not shown) via port #1 of the multi-position distribution valve 9. As will be explained in detail below, the diluter pump 7 is controlled to discharge a sample of blood together with a volume of saline into a first well 10 as part of a first dilution step in the sampling process.

In a second dilution step, the diluter pump 7 draws a dilute sample of blood from the first well 10 via multi-position distribution valve 11 into PTFE fluid line 12 and discharges this sample together with an additional volume of saline into a second well 13. The second well 13 provides the dilute sample source for the gradient generator section 2 described in detail below.

Instead of using whole blood, a pre-diluted sample of blood 14 in a sample container 15 may be used. In this case, a sample probe 16 is connected along PTFE fluid line 30, multi-position distribution valve 11, PTFE fluid line 12 and multi-position distribution value 9 to the diluter pump 7. In a second dilution step, the diluter pump 7 draws a volume of the pre-diluted sample 14 from the sample container 15 via fluid line 30 and multi-position distribution value 11 into fluid line. 12 and discharges the sample together with an additional volume of saline into the second well 13 to provide the dilute sample source for the gradient generator section 2.

The gradient generator section 2 comprises a first fluid delivery syringe 17 which draws water from a supply via multi-position distribution valve 18 and discharges water to a mixing chamber 19 along PTFE fluid line 20. The gradient generator section 2 also comprises a second fluid delivery syringe 21 which draws the diluted sample of blood from the second well 13 in the sample preparation section 1 via multi-position distribution valve 22 and discharges this to the mixing chamber 19 along PTFE fluid line 23 where it is mixed with the water from the first fluid delivery syringe 17. As will be explained in detail below, the rate of discharge of water from the first fluid delivery syringe 17 and the rate of discharge of dilute blood sample from the second fluid delivery syringe 21 to the mixing chamber is controlled to produce a predetermined concentration profile of the sample suspension which exits the mixing chamber 19 along PTFE fluid line 24. Fluid line 24 is typically up to 3 metres long. A suitable gradient generator is described in detail in the Applicant's co-pending International application also filed this day WO 97/24529.

As will also be explained in detail below, the sample suspension exits the mixing chamber 19 along fluid line 24 and enters the sensor section 3 where it passes a sensing zone 25 which detects individual cells of the sample suspension before the sample is disposed of via a number of waste outlets.

In a routine test, the entire system is first flushed and primed with saline, as appropriate, to clean the instrument, remove pockets of air and debris, and reduce carry-over.

The diluter pump 7 comprises a fluid delivery syringe driven by a stepper motor (not shown) and is typically arranged initially to draw 5 to 10 ml of saline from a saline reservoir (not shown) via port #1 of multi-position distribution valve 9 into the syringe body. A suitable fluid delivery syringe and stepper motor arrangement is described in detail in the Applicant's co-pending application also filed this day WO 97/24797. Port #1 of the multi-position distribution valve 9 is then closed and port #0 of both multi-position distribution valve 9 and multi-position distribution valve 8 are opened. Typically 100 µl of whole blood is then drawn from the sample container 5 to take up the dead space in the fluid line 26. Port #0 of multi-position distribution valve 8 is then closed and any blood from the whole blood sample 4 which has been drawn into a fluid line 27 is discharged by the diluter pump 7 to waste via port #1 of multi-position distribution valve 8.

In a first dilution step, port #0 of multi-position distribution value 8 is opened and the diluter pump 7 draws a known volume of whole blood, typically 1 to 20 µl, into PTFE fluid line 27. Port #0 is then closed, port #2 opened and the diluter pump 7 discharges the blood sample in fluid line 27 together with a known volume of saline in fluid line 27, typically 0.1 to 2 ml, into the first well 10. Port #2 of multi-position distribution value 8 and port #0 of multi-position distribution value 9 are then closed.

Following this, port #0 of multi-position distribution valve 11 and port #3 of multi-position distribution valve 9 are opened to allow the diluter pump 7 to draw the first sample dilution held in the first well 10 to take up the dead space in PTFE fluid line 28. Port #0 of multi-position distribution valve 11 is then closed and port #1 opened to allow the diluter pump 7 to discharge any of the first sample dilution which has been drawn into fluid line 12 to waste via port #1.

In a second dilution step, port #0 of multi-position distribution valve 11 is re-opened and the diluter pump 7 draws a known volume, typically 1 to 20 µl, of the first sample dilution into fluid line 12. Fluid line 12 includes a delay coil 29 which provides a reservoir to prevent the sample contaminating the diluter pump 7. Port #0 of multi-position distribution valve 11 is then closed, port #3 opened, and the diluter pump 7 then discharges the first sample dilution in fluid line 12, together with a known volume of saline, typically 0.1 to 20 ml, into the second well 13. Port #3 of multi-position distribution valve 11 is then closed. At this stage, the whole blood sample has been diluted by a ratio of typically 10000:1. As will be explained below, the instrument is arranged automatically to control the second dilution step to vary the dilution of the sample suspension to achieve a predetermined cell count to within a predetermined tolerance at the start of a test routine.

In the gradient generator section 2, the first fluid delivery syringe 17 is primed with water from a water reservoir. Port #3 of multi-position distribution valve 22 is opened and the second fluid delivery syringe draws a volume of the dilute blood sample from the second well 13 into the syringe body. Port #3 of multi-position distribution valve 22 is then closed and port #2 of both multi-position distribution valve 18 and multi-position distribution valve 22 are opened prior to the controlled discharge of water and dilute blood sample simultaneously into the mixing chamber 19.

FIG. 2 shows how the velocity of the fluid discharged from each of the first and second fluid delivery syringes is varied with time to achieve a predetermined continuous gradient of osmolality of the sample suspension exiting the mixing chamber 19 along fluid line 24. The flow rate of the sample suspension is typically in the region of 200 $\mu l\ s^{-1}$ which is maintained constant whilst measurements are being made. This feature is described in detail in the Applicant's co-pending application WO 97/24529. As shown in FIG. 2, a cam profile associated with a cam which drives fluid delivery syringe 21 accelerates the syringe plunger to discharge the sample at a velocity $V_1$, whilst a cam profile associated with a cam which drives fluid delivery syringe 17 accelerates the associated syringe plunger to discharge fluid at a lower velocity $V_2$. Once a constant flow rate from each delivery syringe has been established at time $T_0$, at time $T_1$, the cam profile associated with fluid delivery syringe 21 causes the rate of sample discharge to decelerate linearly over the period $T_2-T_1$ to a velocity $V_2$, while simultaneously, the cam profile associated with fluid delivery syringe 17 causes the rate of fluid discharge to accelerate linearly to velocity $V_1$. During this period, the combined flow rate of the two syringes remains substantially constant at around 200 $\mu ls^{-1}$ Finally, the two syringes are flushed over the period $T_3-T_2$.

Once both the first fluid delivery syringe 17 and the second fluid delivery syringe 21 have discharged their contents, the first delivery syringe is refilled with water in preparation for the next test. If a blood sample from a different subject is to be used, the second fluid delivery syringe 21 is flushed with saline from a saline supply via port #1 of multi-position distribution valve 22 to clean the contaminated body of the syringe.

The sample suspension which exits the mixing chamber 19 passes along fluid line 24 to the sensor section 3. A suitable sensor section is described in detail in the Applicant's co-pending International application also filed this day WO 97/24600. The sample suspension passes to a sensing zone 25 comprising an electrical field generated adjacent an aperture through which the individual cells of the sample suspension must pass. As individual blood cells of the sample suspension pass through the aperture the response of the electrical field to the electrical resistance of each individual cell is recorded as a voltage pulse. The amplitude of each voltage pulse together with the total number of voltage pulses for a particular interrupt period, typically 0.2 seconds, is also recorded and stored for subsequent analysis including a comparison with the osmolality of the sample suspension at that instant which is measured simultaneously. The osmolality of the sample suspension may also be determined without measurement from a knowledge of the predetermined continuous osmotic gradient generated by the gradient generator section 2. As described below, the osmolality (pressure) is not required to determine the cell parameters.

FIG. 3 shows how data is collected and processed. Inside each instrument is a main microprocessor which is responsible for supervising and controlling the instrument, with dedicated hardware or low-cost embedded controllers responsible for specific jobs within the instrument, such as operating diluters, valves, and stepper motors or digitizing and transferring a pulse to buffer memory. The software which runs the instrument is written in C and assembly code and is slightly less than 32 K long.

When a sample is being tested, the amplitude and length of each voltage pulse produced by the sensor is digitized to 12-bit precision and stored in one of two 16K buffers, along with the sum of the amplitudes, the sum of the lengths, and the number of pulses tested. Whilst the instrument is collecting data for the sensors, one buffer is filled with the digitized values while the main microprocessor empties and processes the full buffer. This processing consists of filtering out unwanted pulses, analysing the data to alter the control of the instrument and finally compressing the data before it is sent to the personal computer for complex analysis.

Optional processing performed by the instrument includes digital signal processing of each sensor pulse so as to improve filtering, improve the accuracy of the peak detection and to provide more information about the shape and size of the pulses. Such digital signal processing produces about 25 16-bit values per cell, generating about 25 megabytes of data per test.

Data processing in the personal computer consists of a custom 400K program written in C and Pascal. The PC displays and analyses the data in real time, controls the user interface (windows, menus, etc.) and stores and prints each sample.

The software also maintains a database of every sample tested enabling rapid comparison of any sample which has been previously tested. Additionally, the software monitors the instrument's operation to detect malfunctions and errors, such as low fluid levels, system crashes or the user forgetting to turn the instrument on.

The voltage pulse generated by each cell of the sample suspension as it passes through the aperture of sensing zone 25 is displayed in graphical form on a VDU of a PC as a plot of osmolality against measured voltage. The sample suspension passes through the sensor section at a rate of 200 $\mu ls^{-1}$. The second dilution step is controlled to achieve an initial cell count of around 5000 cells per second, measured at the start of any test, so that in an interrupt period of 0.20 seconds, around 1000 cells are detected and measured. This is achieved by varying automatically the volume of saline discharged by the diluter pump 7 from the fluid line 12 in the second dilution step. Over a test period of 40 seconds, a total of 200 interrupt periods occur and this can be displayed as a continuous curve in a three-dimensional form to illustrate the frequency distribution of measured voltage at any particular osmolality, an example of which is shown in FIGS. 4 and 5.

The measured cell voltage, stored and retrieved on an individual cell basis is shown displayed on a plot of voltage against the osmolality of the solution causing that voltage change. Using individual dots to display the measured parameter change for each individual cell results in a display whereby the distribution of cells by voltage, and thereby by volume, in the population is shown for the whole range of solutions covered by the osmolality gradient. The total effect is a three-dimensional display shown as a measured property change in terms of the amplitude of the measured voltage pulses against altered parameter, in this case the osmolality of the solution, to which the cells have been subjected and the distribution or density of the cells of particular sizes within the population subjected to the particular osmolality. The effect is to produce a display analogous to a contour map, which can be intensified by using colour to indicate the areas of greatest intensity.

When full data is available on the distribution of cell size in a particular population of cells subjected to haemolytic shock in a wide range of hypotonic solutions, at osmolalities just below a critical osmolality causing lysis a gap in the populations is visible. As shown in FIG. 4, ghost cells are fully visible or identifiable in the three-dimensional plot and the unruptured cells are clearly identifiable, but between them is a region defined by osmolality and cell volume where relatively few individuals appear. The existence of this phenomenon, which we have termed the "ghost gap", has not previously been recognised.

If the entire series of steps are repeated at timed intervals on further aliquots of the original sample and the resulting measured voltage is plotted against osmolality, time and frequency distribution, a four-dimensional display, is obtained which may be likened to a change in weather map. This moving three-dimensional display, its motion in time being the fourth dimension, provides an additional pattern characteristic of a particular blood sample. This is shown in the series of images in FIG. 6. The images shown in FIG. 6 are the results of tests carried out at hourly intervals at a temperature of 37° C. As the measurements are so exact, the repeat values are superimposable using computer sequencing techniques.

As shown, cells slowly lose their ability to function over time, but they also change in unexpected ways. The size and shape of the cells in a blood sample change in a complex, non-linear but repeatable way, repeating some of the characteristic patterns over the course of days and on successive testing. The patterns, emerging over time, show similarity among like samples and often show a characteristic wave motion. The pattern of change may vary between individuals reflecting the health of the individual, or the pattern may vary within a sample. Thus a sample that is homogeneous when first tested may split into two or several sub-populations which change with time and their existence can be detected by subjecting the sample to a wide range of different tonicities and recording the voltage pulse in the way described. As shown in FIG. 6, after the first few hours the cell becomes increasingly spherical in the original sample, it then becomes flatter for several hours, then more spherical again, reaches a limit, and then becomes thinner and finally may swell again. It has been determined that the rate at which observed changes take place are influenced by pH, temperature, available energy and other factors.

The three-dimensional pattern provides data which enables identification of the precise osmolality at which particular cells reach their maximum volume, when they become spheres. With appropriate calibration, which is described in detail below, and using the magnitude of the voltage pulse, it is possible to define precisely and accurately the actual volume of such cells and thereafter derive a number of other cell parameters of clinical interest.

The amplitude of the voltage pulses produced by the sensor 25 as individual cells pass through the electrical field are proportional to the volume of each cell. However, before a conversion can be performed to provide a measure of cell volume, the instrument requires calibration. This is performed using spherical latex particles of known volume and by comparison with cell volumes determined using conventional techniques.

Experimental results have shown that the mapping of measured voltage to spherical volume of commercially available latex particles is a linear function. Accordingly, only a single size of spherical latex particles needs to be used to determine the correct conversion factor. In a first calibration step, a sample containing latex particles manufactured by Bangs Laboratories Inc. having a diameter of 5.06 $\mu$m i.e. a volume 67,8344$\mu$m$^3$, was sampled by the instrument. The three-dimensional plot for the latex particles is shown in FIG. 7 with a plot of osmolality against mean voltage shown in FIG. 8. In this particular test, the instrument produced a mean voltage of 691.97 mV. The spherical volume is given by the equation:

Spherical volume=measured voltage×$K_{volts}$ where $K_{volts}$ is the voltage conversion factor.

Re-arranging this equation gives:

$$K_{volts} = \frac{\text{spherical volume}}{\text{measured voltage}}$$

which in this case gives, $$K_{volts} = \frac{67.834}{691.97} = 0.0980$$

This value of $K_{volts}$ is only valid for the particular instrument tested and is stored in a memory within the instrument.

In a second calibration step, a shape correction factor is determined to take account of the fact that the average blood cell in the average individual has a bi-concave shape. Applying the above voltage conversion factor $K_{volts}$ assumes that, like the latex particles, blood cells are spherical and would therefore give an incorrect cell volume for cell shapes other than spherical. In the present invention, a variable shape correction function is determined so that the mean volume of the blood cells at any osmolality up to the critical osmolality causing lysis can be calculated extremely accurately.

To illustrate this, a sample was tested at a number of accurately known osmolalities and the volume of the blood cells measured using a standard reference method, packed cell volume. A portion of the same sample was also tested by the method of the present invention using the instrument of FIG. 1 to measure the voltage pulses from individual cells at the corresponding osmolalities. The results of these procedures are shown in Table 1 and plotted as two superimposed graphs of osmolality (x-axis) against measured voltage and true volume, respectively, in FIG. 9. At an isotonic osmolality of 290 mosm, the true volume, as determined by the packed cell volume technique, was 92.0 fl, whilst the measured mean voltage was 670 mV.

The true isotonic volume of the cells is given by equation:

Volume$_{iso}$=Voltage$_{iso}$×$K_{volts}$ ×$K_{shape}$ where Voltage$_{iso}$ is the measured voltage and $K_{shape}$ is a shape correction factor.

Re-arranging:

$$K_{shape} = \frac{Volume_{iso}}{Voltage_{iso} \times K_{volts}}$$

which in this example gives, $$K_{shape} = \frac{92.0}{670 \times 0.0980} = 1.4$$

Table 1 shows the shape correction factor $K_{shape}$ for each of the other aliquots and demonstrates that the factor to be applied to each sample is different with the maximum shape correction being applied at isotonic osmolalities where the blood cells are bi-concave rather than spherical. To automate the calculation of $K_{shape}$ at any osmolality of interest a shape correction function is required. The following general function describes a shape correction factor based on any two sensor readings i.e. measured voltages:

f($K_{shape}$)=f(SR1, SR2)

where SR1 is a sensor reading (measured voltage) at a known shape, typically spherical, and SR2 is a sensor reading (measured voltage) at an osmolality of interest, typically isotonic.

Analysis has shown that this is a linear function and that:

$$f(K_{shape}) = 1 + \left[\frac{(SR1 - SR2)}{(SR1)}\right] \times K_a$$

where $K_a$ is an apparatus dependent constant, which is determined as follows:

$K_{shape}$ at an osmolality of 290 mosm is known (see above), applying the values SR1=1432 mV, SR2=670 mV and $K_{shape}$=1.4 to the above equation gives:

$$1.4 = 1 + \left[\frac{(1432 - 670)}{1432}\right] \times K_a$$

re-arranging:

$K_a$=0.7518

This value of $K_a$ is constant for this instrument.

The true isotonic volume of a blood sample is determined by comparing the measured voltage at an isotonic volume of interest with the measured voltage of cells of the same blood sample at some known or identifiable shape, most conveniently cells which have adopted a spherical shape, whereby:

$$\text{Volume}_{iso} = \text{Voltage}_{iso} \times K_{volts} \times f(K_{shap})$$

$$= SR2 \times 0.0980 \times \left[1 + \left[\frac{(SR1 - SR2)}{SR1}\right] \times 0.7518\right]$$

In the present invention, the point at which the blood cells become spherical when subjected to a predetermined continuous osmotic gradient can be determined very accurately. FIGS. 10a–10d show the results for a normal blood sample from a healthy individual. FIG. 10a shows a three-dimensional plot of measured voltage against osmolality, FIG. 10b shows a graph of osmolality against percentage change in measured voltage for a series of tests of a sample, FIG. 10c shows the results in a tabulated form, and FIG. 10d shows superimposed graphs of mean voltage and cell count for the test, respectively, against osmolality. As shown, the cell count, which is initially 5000 cells per second at the beginning of a test, reduces throughout the test due to the dilution of the sample in the gradient generator section 2. The mean voltage rises to a maximum at a critical osmolality where the blood cells achieve a spherical shape and then reduces. Using standard statistical techniques, the maxima of the curve in FIG. 10b, and therefore the mean voltage at the maxima, can be determined. The mean voltage at this point gives the value SRi for the above equation. It is then possible to select any osmolality of interest, and the associated measured voltage SR2, and calculate the true volume of the cell at that osmolality. Typically, the isotonic osmolality is chosen, corresponding to approximately 290mosm.

For the above test, at 290 mosm, SR1=1432 mV and SR2=670 mV. Accordingly:

$$f(K_{shape90}) = 1 + \left[\frac{1432 - 670}{1432}\right] \times 0.7518$$

$K_{shape}$ 290=1.40 and therefore:

$$\text{Volume}_{iso} = SR2 \times K_{volts} \times K_{shape}$$

$$= 670 \times 0.0980 \times 1.40$$

$$= 91.92 \text{ fl},$$

and:

$$\text{Volume}_{sph} = SR1 \times K_{volts} \times K_{shape}$$

$$= 1432 \times 0.098 \times 1.0$$

$$= 140.34 \text{ fl}.$$

Knowledge of the mean volume of the sphered cells allows calculation of spherical radius as:

$$\text{Volume}_{sph} = \frac{4\pi r^3}{3}$$

from which the spherical radius $$r = \left[\frac{3 \times \text{Volume}_{sph}}{4\pi}\right]^{\frac{1}{3}}$$

$$r = \left[\frac{3 \times 140.34}{4\pi}\right]^{\frac{1}{3}}$$

$$= 3.22 \, \mu\text{m}$$

Having determined volume$_{iso}$, volume$_{sph}$ and the spherical cell radius, it is possible to calculate a number of other parameters. In particular:

1. Surface Area (SA)

Since the surface area SA is virtually unchanged at all osmolalities, the cell membrane being virtually inelastic, and in particular between spherical and isotonic, the surface area SA may be calculated by substituting r into the expression:

$$SA = 4\pi r^2$$

$$= 4\pi \times (3.22)^2$$

$$= 130.29 \, \mu\text{m}^2$$

2. Surface Area to Volume Ratio (SAVR) Given that the walls of a red cell can be deformed without altering their area, once the surface area SA is known for a cell or set of cells of any particular shape, the surface area is known for any other shape, thus the surface area to volume ratio SAVR can be calculated for any volume. SAVR is given by the expression:

$$SAVR = \frac{4\pi r^2}{\text{Volume}_{iso}} = \frac{SA}{\text{Volume}_{iso}}$$

$$= \frac{130.29}{91.99}$$

$$= 1.42$$

3. Sphericity Index (SI)

The present invention can easily measure the SAVR, a widely quoted but hitherto, rarely measured indication of cell shape. For a spherical cell, it has the value of 3/r, but since cells of the same shape but of different sizes may have different SAVR values, it is desirable to use the sphericity index SI which is a dimensionless unit independent of cell size, given by the expression:

$$SI = SAVR \times \frac{r}{3}$$
$$= 1.42 \times \frac{3.22}{3}$$
$$= 1.52$$

4. Cell Diameter (D)

When the normal cell is in the form of a bi-concave disc at isotonic osmolality, it is known that the ratio of the radius of a sphere to that of the bi-concave disc is 0.8155. On this basis, therefore, the diameter D of a cell in the form of a bi-concave disc is given by:

$$D = \frac{2r}{0.8155}$$
$$= \frac{2 \times 3.22}{0.8155}$$
$$= 8.19 \mu m$$

The same parameter can be determined for all other osmolalities. The frequency distribution of the cell diameters is given both as dispersion statistics as well as a frequency distribution plot. The present invention provides an automated version of the known manual procedure of plotting a frequency distribution of isotonic cell diameters known as a Price-Jones curve. The present invention is capable of producing a Price-Jones curve of cell diameters for any shape of cell and, in particular, isotonic, spherical and ghost cells (at any osmolality) and is typically based on 250,000 cells. This is shown in FIG. 10.

5. Cell Thickness (CT)

When the cell is in the form of a bi-concave disc, an approximate measure of the cell thickness can be derived from the cross-sectional area and the volume. The area is of course derivable from the radius of the cell in spherical form. The cell thickness can therefore be calculated as follows:

$$CT = \frac{Volume_{iso}}{\pi r^2}$$
$$= \frac{91.92}{\pi \times 3.22^2}$$
$$= 2.82 \mu m$$

6. Surface Area per millilitre (SAml)

The product of the surface area (SA) and the cell count (RBC) is the surface area per millilitre (SAml) available for physiological exchange. Typically, a healthy adult male has a value of 1,000,000 mm²/ml, or 1m²/ml. The total surface area of the proximal renal tubes that are responsible for acid-base regulation of the body fluids is 5 m². The total surface area of the red blood cells that also play an important part in the regulation of the acid-base balance is 4572 m$_{hu}$2, almost 3 orders of magnitude larger. RBC is calculated internally from a knowledge of the flow rate of the diluted blood sample, a cell count for each sample and the dilution of the original whole blood sample. Typically, RBC is approximately $4.29 \times 10^9$ red cells per ml.

$$SAml = SA \times RBC \text{ (per ml)}$$
$$= 130.29 \mu m^2 \times 4.29 \times 10^9 \text{ per ml}$$
$$= 0.56 \, m^2 \, ml^{-1}$$

The above parameters are calculated and displayed along with the characteristic curve of osmolality against percentage change in voltage in FIG. 10b.

FIG. 12 illustrates the three-dimensional frequency distribution of a sample from a patient having an HbCC disease. As shown, the plot is grossly abnormal.

What is claimed is:

1. A method in which a sample of cells suspended in a liquid medium, wherein the cells have at least one measurable property distinct from that of the liquid medium, is subjected to analysis by a method including the steps of:
    (a) passing a first aliquot of the sample cell suspension through a sensor,
    (b) measuring said at least one property of the cell suspension,
    (c) recording the measurement of said property for the first aliquot of cells;
    (d) subjecting the first or at least one other aliquot of the sample cell suspension to an alteration in at least one parameter of the cell environment which has the potential to alter the shape of the cells in the sample to a known or identifiable extent to create an altered cell suspension,
    (e) passing said altered cell suspension through a sensor,
    (f) measuring said at least one property of the altered cell suspension,
    (g) recording the measurement of said at least one property for said altered suspension,
    (h) comparing the data from steps (c) and (g) and determining a sample specific cell shape compensation factor,
    (i) applying the cell shape compensation factor to the measurement of said at least one property of the first aliquot of cells in step (c) in the calculation of a cell parameter, so as to take account of a variation in cell shape between the first aliquot of cells in step (c) and said altered cell suspension in step (g).

2. A method according to claim 1, in which the property of the cells which differs from the liquid medium is one which is related to the volume of the cell.

3. A method according to claim 1, in which the cell property is electrical resistance or impedance.

4. A method according to claim 1, in which the environmental parameter change is an alteration in osmolality.

5. A method according to claim 1 in which the environmental parameter change is an alteration in osmolality, and wherein the shape compensation factor determined in step (g) is given by the expression:

$$f(K_{shape}) = 1 + \left[ \frac{(SR1 - SR2)}{(SR1)} \right] \times K_a$$

where K shape is the shape compensation factor, SR1 is a sensor reading at a known or identifiable shape, SR2 is a sensor reading at an osmolality of interest, and Ka is an apparatus dependent constant.

6. A method according to claim 5, in which the sensor reading is one of voltage amplitude.

7. A method according to claim 6, in which the volume of a cell at an osmolality of interest is determined from the expression:

$$\text{Cell Volume} = SRn \times K_{volts} \times K_{shape}$$

where SRn is a sensor reading at the osmolality of interest, $K_{volts}$ is a predetermined voltage to cell volume conversion factor, and $K_{shape}$ is the shape compensation factor determined for the sensor reading SRn.

8. A method according to claim 5, in which said known or identifiable shape is a spherical shape.

9. A method according to claim 1, in which the sample is fed continuously into a solution, the osmolality of which is changed continuously to produce a continuous gradient of aliquots for passage through the sensing zone.

10. A method according to claim 9, in which identical portions of the sample under test are subjected to solutions of each osmolality throughout the range under test after substantially the same time from imposition of the environmental parameter change to the time of passage through the sensing zone.

11. A method according to claim 1, in which said at least one property of the altered cell suspension is measured as each of a number of cells passes through the sensor, the measurement of said at least one property for the altered cell suspension is recorded on a cell-by-cell basis, and the data from steps (c) and (g) is compared as a functions of the extent of said alteration of said parameter of the cell environment and frequency distribution of said at least one property.

12. A method according to claim 11, further comprising the step of displaying the results of the analysis in the form of a three dimensional plot.

13. A method according to claim 1, in which the second aliquot of the sample cell suspension is subjected to an alteration in at least one parameter of the cell environment which has the potential to induce a flow of fluid across the cell member and thereby alter the said at least one property of the cells, wherein data from steps (c) and (g) is compared as a function of the extent of said alteration of said parameter of the cell environment and change in the recorded measurements of said at least one property to determine a measure of cell permeability of the sample.

14. An apparatus for testing a sample cell suspension in a liquid medium in accordance with the method of claim 1, comprising data processing means programmed to compare data from said steps (c) and (g) to determine a shape compensation factor to be applied to the measurement of said at least one property of the first aliquot of cells in the calculation of a cell parameter to take account of a variation in shape between the first aliquot of cells and said altered cell suspension.

15. An apparatus according to claim 14, in which the data processing means is programmed to compare data from steps (c) and (g) on a cell-by-cell basis as a function of the extent of said alteration of said parameter of the cell environment and frequency distribution of said at least one property.

16. An apparatus according to claim 14, in which the data processing means comprises the internal microprocessor of a personal computer.

* * * * *